United States Patent [19]

Combs

[11] Patent Number: 5,684,151
[45] Date of Patent: Nov. 4, 1997

[54] 1-ARYLSULPHONYL, ARYLCARBONYL AND 1-ARYLPHOSPHONYL-3-PHENYL-1,4,5,6-TETRAHYDROPYRIDAZINES

[75] Inventor: Donald W. Combs, Piscataway, N.J.

[73] Assignee: Ortho Pharmaceutical Corporation, Raritan, N.J.

[21] Appl. No.: 362,476

[22] PCT Filed: Jul. 1, 1993

[86] PCT No.: PCT/US93/06394

§ 371 Date: Mar. 6, 1995

§ 102(e) Date: Mar. 6, 1995

[87] PCT Pub. No.: WO94/01412

PCT Pub. Date: Jan. 20, 1994

Related U.S. Application Data

[63] Continuation-in-part of Ser. No. 80,986, Jun. 21, 1993, abandoned, which is a continuation of Ser. No. 906,984, Jul. 1, 1992, abandoned.

[51] Int. Cl.$^6$ .................. C07D 237/04; C07D 409/04; C07D 237/26
[52] U.S. Cl. .................. 544/224; 544/232; 544/235; 544/238; 544/239
[58] Field of Search .................. 544/224, 235, 544/238; 514/247, 252

[56] References Cited

PUBLICATIONS

Clark et al, *Chemical Abstracts*, vol. 104, No. 109560 (1986).
Faragher et al, *J. Chem. Soc. Perkin Trans.* 1, p. 249 (1979).
Hishmat et al, *Arzheim.–Forsch/Drug Res.* 35, pp. 784–786 (1985).
Shabarov et al, *Chemical Abstracts*, vol. 54, No. 14260b (1960).

*Primary Examiner*—Emily Bernhardt

[57] ABSTRACT

Disclosed are progestin agonists having the following formula:

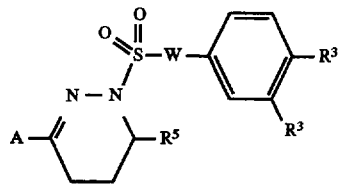

wherein:

A is

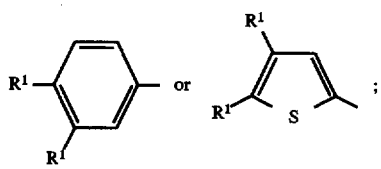

W is absent or —CH=CH—;
$R^1$ are independently selected from the group consisting of halogen, —$CF_3$, and $NO_2$, or both $R^1$ may be joined to form a bi-radical which is —CH=CHCH=CH—;
$R^3$ are independently selected from the group consisting of hydrogen, $C_{1-6}$ branched or linear alkyl, halogen and —$CF_3$, with the proviso that $R^3$ at the 3-position must be H where $R^3$ at the 4-position is H, or both $R^3$ may be joined to form a bi-radical selected from the group consisting of —CH=CHCH=CH—, —C(N$C_{1-4}$alkyl$_2$)=CHCH=CH— and —$(CH_2)_4$—;
$R^5$ is selected from the group consisting of H and Me;
with the proviso that only one of $R^1$ and $R^3$ forms the fused bi-radical; and the stereoisomers.

12 Claims, No Drawings

1-ARYLSULPHONYL, ARYLCARBONYL AND 1-ARYLPHOSPHONYL-3-PHENYL-1,4,5,6-TETRAHYDROPYRIDAZINES

This application is a 371 of PCT/US93/06394 filed Jul. 1, 1993, which is a continuation-in-part of U.S. Ser. No. 08/080,986 filed Jun. 21, 1993, now abandoned, which is a continuation of U.S. Ser. No. 07/906,984, filed Jul. 1, 1992, now abandoned.

FIELD OF THE INVENTION

The invention relates to novel 1-phenylsulphonyl, phenylcarbonyl and 1-phenylphosphenyl-3-phenyl-1,4,5,6-tetrahydropyridazine compounds, and to novel methods for preparing the compounds. The novel compounds are useful as contraceptives and in the treatment of osteoporosis. The invention further relates to pharmaceutical compositions in which a compound of the present invention is the active ingredient.

BACKGROUND OF THE INVENTION

The unacylated 3-phenyl-1,4,5,6-tetrahydropyridazine, A, is described by J.-L. Aubagnac et al., *Bull. Chem. Soc. France*, 7, 2868, (1972). A number of 1-acylated derivatives of 1 are also disclosed.

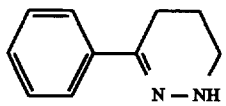

A

W. Jones et al., *J. Het. Chem.*, 21, 889 (1984) disclose that the thiocarbamoylation of A with methyl isothiocyanate produces the corresponding thiocarbamide derivative, B. No biological activity is disclosed.

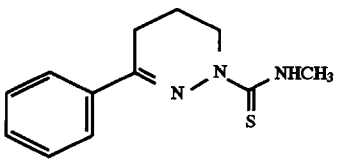

B

S. J. Clarke et al., *J. Chem. Research*, (S) 310 (1985) disclose carbamate, carbamide and para-toulene sulfonamide derivatives of A. (sulfonamide derivative is C), which are prepared via cycloaddition reactions. Again, no biological activity is disclosed.

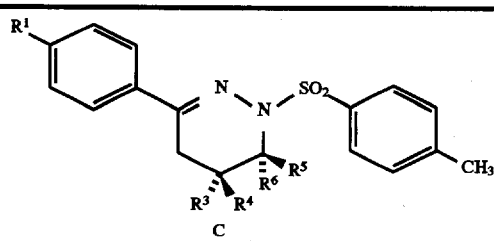

C

| $R^1$ | $R^3$ | $R^4$ | $R^5$ | $R^6$ |
|---|---|---|---|---|
| H | H | H | OEt | H |
| H | H | Me | OEt | H |
| H | Me | H | OEt | H |
| H | H | H | OMe | Me |
| NO$_2$ | H | H | OEt | H |
| NO$_2$ | H | H | OMe | Me |

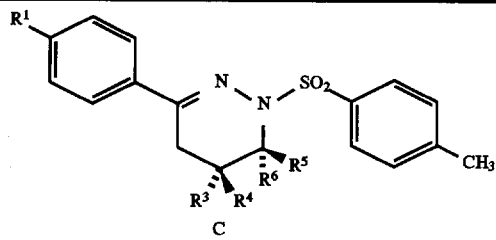

C

| $R^1$ | $R^3$ | $R^4$ | $R^5$ | $R^6$ |
|---|---|---|---|---|
| Br | H | H | OEt | H |
| Br | H | Me | OEt | H |
| Br | Me | H | OEt | H |
| Br | H | H | OMe | Me |

R. Faragher et al., in *J. Chem. Soc. Perkin Trans*, I, 249 (1979), disclose para-toulene sulfonamide and carbamate derivatives of A, (sulfonamide derivative is 4) which compounds are also prepared by cycloaddition reactions. As above, no biological activity is disclosed.

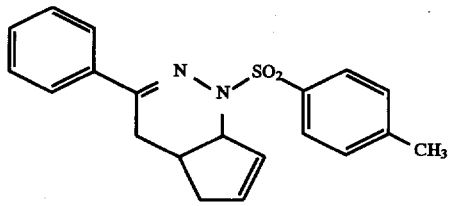

D

Kalyanam et al., *Synthetic Communications*, 18 (16 & 17), (1988) disclose compounds of the formula:

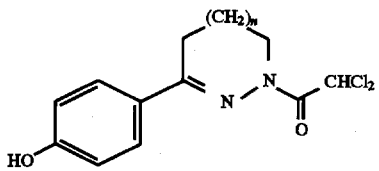

wherein n is 1 or 2, as being antiamoebics.

SUMMARY OF THE INVENTION

Briefly, according to the present invention, there are provided preferred progestin agonists of the general formula:

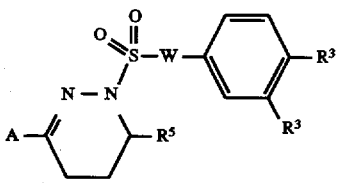

wherein:

A is

-continued

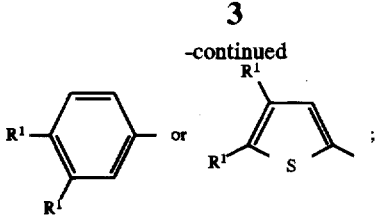

W is absent or —CH=CH—;
R¹ are independently selected from the group consisting of halogen, —CF₃, and NO₂, or both R¹ may be joined to form a bi-radical which is —CH=CHCH=CH—;
R³ are independently selected from the group consisting of hydrogen, $C_{1-6}$ branched or linear alkyl, halogen and —CF₃, with the proviso that R³ at the 3-position must be H where R³ at the 4-position is H, or both R³ may be joined to form a bi-radical selected from the group consisting of —CH=CHCH=CH—, —C(NC$_{1-4}$alkyl$_2$)=CHCH=CH— and —(CH₂)₄—;
R⁵ is selected from the group consisting of H and Me;
with the proviso that only one of R¹ and R³ forms the fused bi-radical; and the stereoisomers.

Also provided by the present invention are preferred progestin antagonists of the general formula:

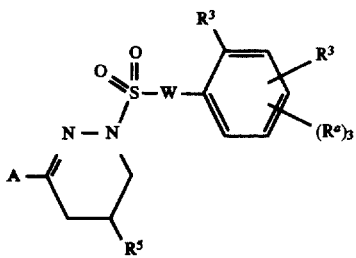

wherein

A is

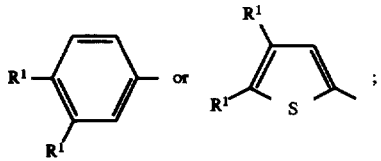

W is absent or —CH=CH—;
R¹ is selected from the group consisting of halogen, —CF₃ and —NO₂, or both R¹ may be joined to form a bi-radical which is —CH=CHCH=CH—;
R³ is hydrogen, halogen, —CF₃, $C_{1-4}$ alkyl, $C_{1-4}$ alkoxy, carboxy $C_{1-4}$ alkyl and $C_{1-4}$ alkoxy carbonyl $C_{1-4}$ alkoxy with the proviso that R³ at the 2-position is not hydrogen, or R³ may be joined to form a bi-radical which is —CH=CHCH=CH— attached at the 2- and 3-positions;
Rᵃ are independently selected from hydrogen or halogen with the proviso that each may be halogen where Rᵃ is selected only from halogen;
R⁵ is selected from the group consisting of hydrogen and methyl, or alternatively, R⁵ may be joined with the 6-position hydrogen to form a bi-radical which is (5)-CH₂CH=CH-(6);
with the proviso that only one of R¹, R³ and R⁵ forms the fused bi-radical; and the steroisomers and pharmaceutically acceptable salts and esters thereof.

Also provided by the present invention are preferred compounds useful to promote bone cell gowth, said compounds having the general formula:

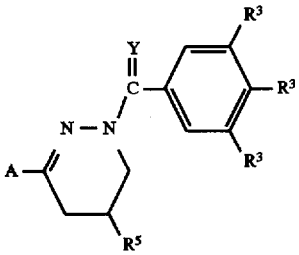

wherein

A is

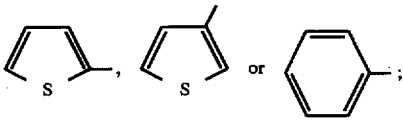

Y is O or S;
R³ is hydrogen or halogen with the proviso that at least two R³ are halogen;
R⁵ is H or Me;
and the steroisomers thereof.

4. DETAILED DESCRIPTION OF THE INVENTION

The compounds of the present invention may be manufactured in what is basically a two step process. In the first step and as demonstrated in schemes 1 and 2, a 3-phenyl-1,4,5,6-tetrahydropyridazine intermediate is formed. In the second step and as demonstrated in scheme 3, this 3-phenyl-1,4,5,6-tetrahydropyridazine intermediate is joined at the 1-position with the appropriately substituted phenyl or thienyl moiety. In special cases, and as exemplified in scheme 4, more advantageous processes are available for certain substitution patterns. Of course, the substituents on the final compounds may be obtained by starting with the appropriately substituted starting materials or by modifying precursor substituents on an intermediate or final compound. Persons skilled in the art upon understanding the particular reactions suggested herein will be readily able to determine how best to obtain a given substituent.

The substituents R¹*, R³* and R⁵* as employed in Schemes 1-4 are intended to include not only the substituents of R¹, R³ and R⁵ as given above for the preferred compounds, but also to include other substituents on their respective rings of compounds disclosed herein. Subscripts w, y and z as employed in these same schemes have values ranging from 0–5, 0–3 and 0–5 respectively and are intended to show that not just the the substitution patterns of the preferred compounds as described above may be made by this method, but that compounds with various substitution patterns may be made. Finally, Schemes 1-4 are exemplified employing phenyl as the ultimate 3-position substituent on 1,4,5,6-tetrahydropyridazine. In each scheme, a starting material in which phenyl is replaced by the appropriate thienyl would ultimately produce, by the same method, a 3-thienyl substituent on the 1,4,5,6-tetrahydropyridazine, Thus, although Schemes 1-4 exemplify the manufacture of the 3-phenyl substituent, the 3-thienyl substituent is similarly produced.

Referring to scheme 1, 3-phenyl-1,4,5,6-tetrahydropyridazine, intermediate 1-C, is formed in two reaction steps, In a first addition reaction, diketone starting material 1-A is refluxed in an alcohol solvent with an excess of hydrazine to give the 6-oxo compound 1-B. Suitable alcohol solvents include methanol, ethanol, etc., with the reflux carried out for from 1 to 24 hours. This addition is further described by S. Gabriel et al., Ber., 32, 395 (1879), W. Curran et al., J. Med. Chem., 17(3), 273 (1974) and in U.S. Pat. Nos. 4,766,118 and 4,721,784, which are incorporated herein by reference. Subsequently, 6-oxo compound 1-B is reduced to intermediate 1-C in the presence of a reducing agent Suitable reducing agents include diborane, lithium aluminum hydride and di-i-butyl aluminum hydride. Where lithium aluminum hydride is employed, the reaction should be carried out at reduced temperatures in a solvent such as THF. This reduction is further described by J. L. Aubagnac et al., Bull. Chem. Soc. France, 2859 (1972). Of course, it is clear that intermediate 1-C cannot have $R_{5*}$ as a 6-position substituent.

SCHEME 1

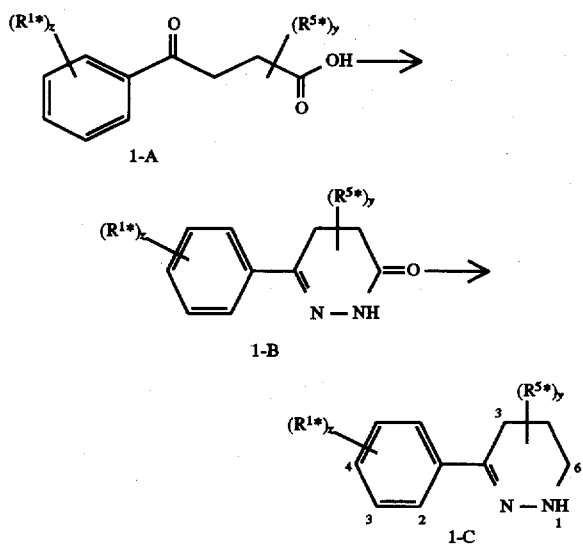

Referring to Scheme 2, 3-phenyl-1,4,5,6-tetrahydropyridazine, intermediate 2-C, is formed in four reaction steps. In a first reaction, the appropriate phosphonium salt is deprotonated in ethereal solvent (ether, tetrahydrofuran, dioxane) with strong base (such as alkyllithium, sodium or potassium hydride or lithium diisopropyl amide) and stirred at low temperature under an atmosphere of inert gas. The aldehyde 2-A is added to the cold solution and the mixture stirred for several hours at room temperature. Excess reagent is quenched (with water or an alcohol), and the solution is filtered, dried over $Na_2SO_4$ (or $MgSO_4$, $CaCl_2$, $CaSO_4$, $K_2CO_3$, or other similar drying agent), filtered again, and solvent is removed to give the diene 2-A' which is used without further purification. In a second step, 4-phenylurazole is dissolved in DMSO and cooled in a dry apparatus. Tosylisocyanate is added as an oxidant and stirring continued. The diene 2-A' is added neat and the reaction continued for about 30 min. The solution is poured into a halogenated solvent (chloroform, carbon tetrachloride, methylene chloride, dichloroethane) and washed with aqueous base (such as a solution of NaOH, KOH, $NaHCO_3$, $Na_2CO_3$ or $K_2CO_3$). The solution is dried over $Na_2SO_4$ (or $MgSO_4$, $CaCl_2$, $CaSO_4$, $K_2CO_3$, or other similar drying agent) and the solvent is removed to give 2-B. In a third step, reduction of 2-B is effected by shaking with $H_2$ gas (1–3 atm) and Pd/C (5–10%) in an organic solvent such as ethanol, ethyl acetate, acetic acid or tetrahydrofuran until the theoretical amount of hydrogen is consumed. The catalyst is removed by filtration and the solvent is evaporated to give 2-B'. Alternatively, 2-B is reduced in an ethereal solvent (ether, tetrahydrofuran, dioxane) with diborane followed by treatment with a carboxylic acid at elevated temperature. Excess acid is neutralized and the solution is washed. The solution is dried over $Na_2SO_4$ (or $MgSO_4$, $CaCl_2$, $CaSO_4$, $K_2CO_3$, or other similar drying agent), filtered, and solvent removed. In the final step, the urazole 2-B' is hydrolyzed with base such as NaOH, KOH or LiOH in an alcohol solvent such as (methanol, ethanol, ethylene glycol, propylene glycol) at elevated temperatures. Air oxidation to the desired product 2-C occurs spontaneously. The solution is diluted with water, washed with an organic solvent such as ether or methylene chloride and dried over $Na_2SO_4$ (or other similar drying agent), filtered, and the solvent removed. Of course, it is clear that intermediate 2-C might have $R^{5*}$ substituents at any of positions 4,5 and 6.

SCHEME 2

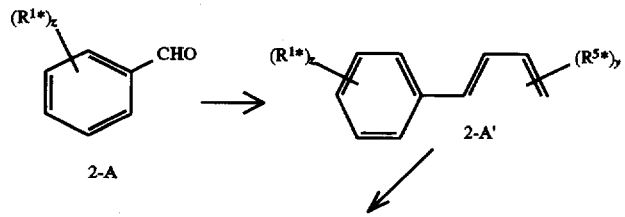

-continued
SCHEME 2

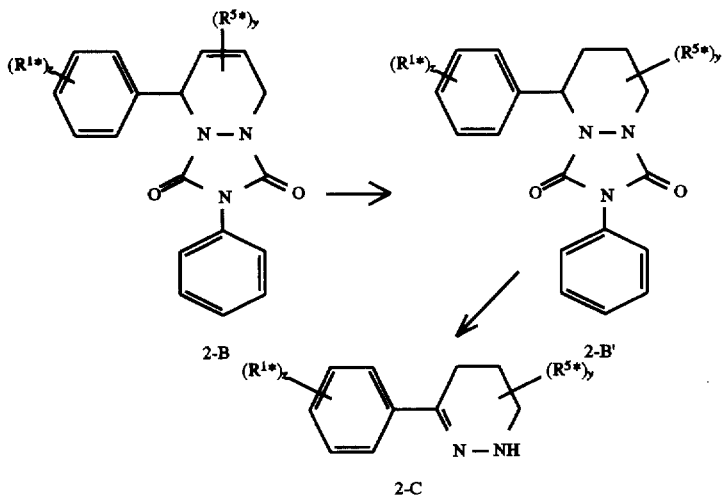

Referring to Scheme 3, intermediate 1-C or 2-C is converted to final product in a one step acylation. In the arylation reaction, appropriately substituted 3-aryl-1,4,5,6-tetrahydropyddazine, intermediate 1-C or 2-C, is added with the appropriate acylating agent, i.e., phenyl carbonyl halide, phenyl sulphonyl halide or phenyl phosphonyl dihalide, to an organic base such as pyridine or collidine, or to an organic solvent such as THF, methylene chloride or toluene with a base such as DMAP or triethylamine, or to an aqueous base such as sodium or potassium hydroxide.

SCHEME 3

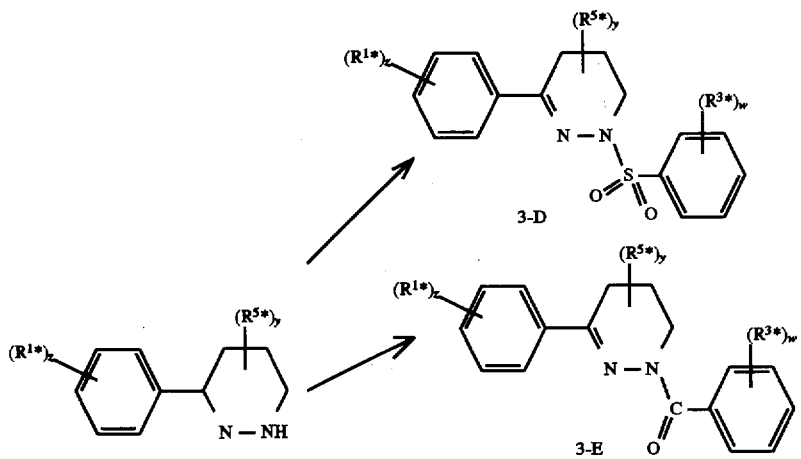

-continued
SCHEME 3

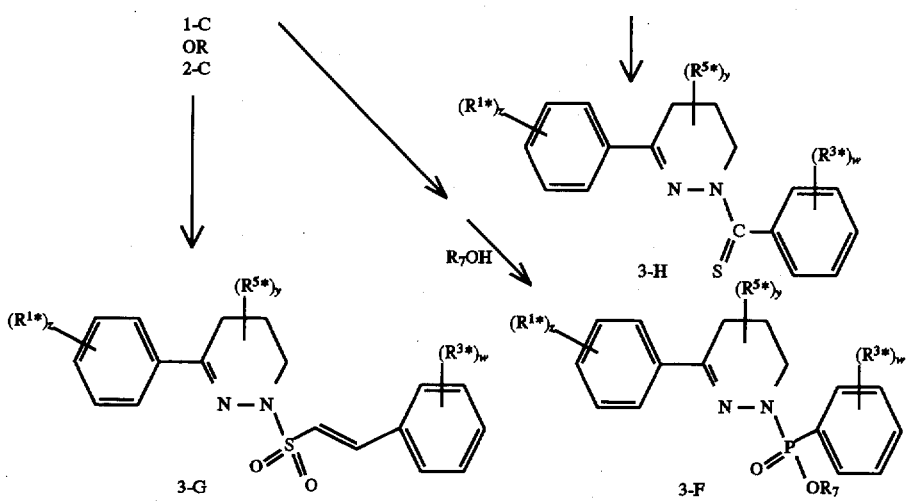

In the case of the reaction employing an phenylphosphonyl dihalide, an alcohol such as methanol, ethanol, propanol, isopropanol, cyclopentanol or phenol is added after the reaction of the tetrahydropyridazine with the phenylphosphonyl dihalide. The halide portion of the acylating agent may be any reactive halide but preferred are chloro or bromo. The product is isolated by pouring the reaction mixture into dilute acid solution such as a hydrobromic or a hydrochloric acid solution and extracting with an organic solvent such as methylene chloride or ethyl acetate. The organic layer is then concentrated, and the residue recrystallized or chromatographed using for example methylene chloride and/or ether and/or ethyl acetate and/or methanol on silica gel. The fractions containing the product are evaporated and the residue recrystallized from an appropriate solvent such as acetone, ether, ethyl acetate, methanol, or hexane to afford the desired acylated compounds 3-D to 3-G.

For example, to prepare the arylsulphonyltetrahydropyridazines 3-D, the appropriate phenylsulfonyl chloride is added at about room temperature to a solution of the appropriate intermediate 1-C or 2-C in an organic solvent such as pyridine or a solution of 4-N,N-dimethylaminopyridine in methylene chloride, and the resulting mixture is stirred for about 1 to about 72 hours. The reaction mixture is then treated with an acidic solution such as dilute to 6N HCl or HBr, followed by successive washes with an organic solvent such as chloroform or methylene chloride. The combined organic extracts are dried with a drying agent such as sodium sulfate, magnesium sulfate or potassium carbonate, concentrated and chromatographed using for example methylene chloride and/or ether and/or ethyl acetate and/or methanol on silica gel. The desired fractions are recrystallized from a suitable organic solvent Such as ether, ethyl acetate, methanol or hexane to yield the desired phenylsulphonyltetrahydropyridazine 3-D.

Several general procedures are used for the preparation of the phenylcarbonyltetrahydropyridazines 3-E. For example, an appropriate phenylcarbonyl halide is added to a solution of the intermediate 1-C or 2-C in an organic solvent such as dichloromethane or toluene. The resulting mixture is heated to reflux for about 1 to about 4 hours, optionally stirred at about room temperature for about 16 hours, dried and concentrated. Column chromatography employing for example methylene chloride and/or ether and/or ethyl acetate and/or methanol on silica gel is then performed on the residue, followed by recrystallization of the desired fractions from a suitable solvent such as ether, ethyl acetate, methanol or hexane to yield the desired phenylcarbonyltetrahydropyridazine 3-E. In another example, an appropriate phenylcarbonyl is added to a solution of the appropriate intermediate 1-C or 2-C in an organic solvent such as collidine or pyridine. The resulting mixture is stirred at about room temperature for about 1 to about 72 hours, dried and concentrated. The isolation of the phenylcarbonyltetrahydropyridazine 3-E is undertaken as noted previously. In yet another example, an appropriate phenylcarbonyl chloride is added to a stirred solution of the intermediate 1-C or 2-C in an organic solvent such as toluene or methylene chloride at about room temperature under an dry atmospheric conditions such as argon or $N_2$. A tertiary amine such as dimethylaminopyridine or triethylamine is added to the mixture and the progress of the reaction is monitored by TLC. The isolation of the phenylcarbonyltetrahydropyridazine 3-E which is prepared under these conditions is undertaken as noted previously. The following general procedure is used for the preparation of the phenylphosphonyltetrahydropyridazines 3-F. For example an phenylphosphonyl dihalide such as 4-methoxyphenylphosphonic dichloride, 4-chlorophenyl-phosphonic dichloride or phenylphosphonic dichloride is added (preferably dropwise) to a solution of the appropriate intermediate 1-C or 2-C in an organic solvent such as collidine or pyridine at about 0° C. The reaction mixture is stirred at about 0° C. for about 1 hour, and then warmed to about room temperature. An appropriate alcohol of the formula $R_7OH$ and including ethanol, methanol, propanol, butanol, cyclopentanol, isopropanol or phenol, is added to the resulting mixture and this mixture stirred at about room temperature for about 16 hours. The work-up of the reaction mixture and the isolation of the phenylphosphonyltetrahydropyridazine 3-F is effected in the same manner as noted previously regarding the phenylsulphonyltetrahydropyridazines.

The appropriate acylating agents are well known to persons skilled in the art and may be prepared as follows: benzenesulphonylhalide; (Beilstein 11, 34; phenylethenylsulphonyl halide, M. Culbertson, et al., J. Chem. Soc. (C) 992, (1968) and Beilstein 11, 2; phenylmethylsulphonylhalide, Beilstein 11, 116;

benzoylhalide, Beilstein 9, 182; phenylacetylhalide, Beilstein 9, 436; cinnamoylhalide, Beilstein 9, 587; and phenylphosphonyldihalide, Beilstein 16, 804.

Scheme 3 shows the following general procedure used for the preparation of the phenylthiocarbonyltetrahydropyridazines 3-H. For example, a sulfurization agent such as Lawesons reagent or phosphorous pentasulfide is added to a solution of an appropriate phenylcarbonyltetrahydropyridazine 3-E in an inert organic solvent such as benzene or toluene. The mixture is heated to reflux under dry atmospheric conditions such as argon or $N_2$ for about 2 hours, filtered and concentrated. The work-up of the reaction mixture and the isolation of the phenylthiocarbonyltetrahydropyridazines 3-H is effected in the same manner as noted previously regarding the phenylcarbonyltetrahydropyridazines.

Referring to Scheme 4, compounds of the present invention in which $R^{5*}$ is a bivalent alkyl or alenyl radical attached at the 5- and 6-position are favorably prepared via a cycloaddition between an appropriate azoalkene and an electron-rich alkene, e.g., dienes, including cyclopentadiene. The azoalkene is generated in situ by: (1) reacting the appropriate phenylsulphonylhydrazide with an appropriate α-bromo- or α-chloro-alkylarylketone, e.g., chloroacetophenone, to yield the corresponding hydrazone 4-A; and (2) treating the hydrazone 4-A with a base such as sodium hydroxide, potassium carbonate, sodium carbonate or sodium bicarbonate to produce final product 4-B. This reaction if further desribed by Clarke et al., J. Chem. Research (S), 310 (1985) and Faragher et al., J. Chem. Soc. Perkin Trans. I, 249 (1979).

For example, a 1-phenylsulphonyl hydrazide is added to a solution of α-chloroacetophenone in an organic solvent such as THF or ether. The mixture is heated to reflux for about 2 hours and then concentrated. Upon cooling to about 0° C., a solid residue is produced. The precipitate is washed with an organic solvent such as ether or hexane and dried to yield the corresponding hydrazone 4-A'. An electron-rich diene or alkene 4-A" (preferably freshly distilled) such as indene, 1-methoxycyclohexene, dicyclopentadiene or cyclopentadiene in an organic solvent such as ether or THF is added to a solution of the hydrazone, followed by the addition of a base such as potassium carbonate or sodium bicarbonate. The mixture is stirred at about room temperature for about 12 hours and then filtered through, for example, florisil or Celite. The filtrate is concentrated. The resulting residue is chilled to about 0° C. and triturated with an alcohol such as methanol or ethanol. A solid is precipitated out of the mixture, collected and washed with an organic solvent such as ether or hexane to yield a compound of the invention 4-B. Where the alkene employed is a diene, a product is produced that has an unsaturated moiety, e.g., $R^{5*}$ fused bi-radical such as —$CH_2$—CH=CH—. The compound having the unsaturated moiety may be treated with $H_2$ and a catalytic amount of a metal such as platinum oxide or palladium on carbon in an alcohol such as isopropanol, methanol or ethanol to yield the corresponding compound wherein the unsaturated bi-radical is hydrogenated (saturated), i.e., the fused bi-radical —$CH_2$—CH=CH— is converted to —$(CH_2)_3$—. The reaction is effected by shaking a suspension of the compound having the unsaturated moiety in a Parr Shaker apparatus under a $H_2$ atmosphere for about 1 to 3 hours, at about 20 to 50 psi, filtering and concentrating. The resulting reduction product is purified by recrystallization from an organic solvent such as ether, hexane, ethanol or ethyl acetate.

An alternate method by which an intermediate of the type of 1-C and 2-C may be made can be found in N. Kalyanam et al., Synthetic Communications, 18 (16 and 17) (1988). In this method, an appropriate intermediate 1-C or 2-C is prepared directly from an appropriate 4-halobutyl aryl ketone.

The invention also pertains to the racemate, individual stereoisomers, and mixtures thereof. The isomers are isolated by standard resolution techniques including fractional crystallization and chiral column chromatography.

The compound of the present invention also include pharmaceutically acceptable salts and esters. Although the acylated tetrahydropyridzines base ring does not form salts or esters, substitutents thereon, which include carboxy or amine groups may. In the case of salts, there are acid addition salts with amine containing substituents and base salts or alkali metal salts with carboxy containing substituents. Suitable acid addition salts may be formed upon the combination of amine containing substituents with chlorides, such as hydrochloride; sulfates, such as hydro-

SCHEME 4

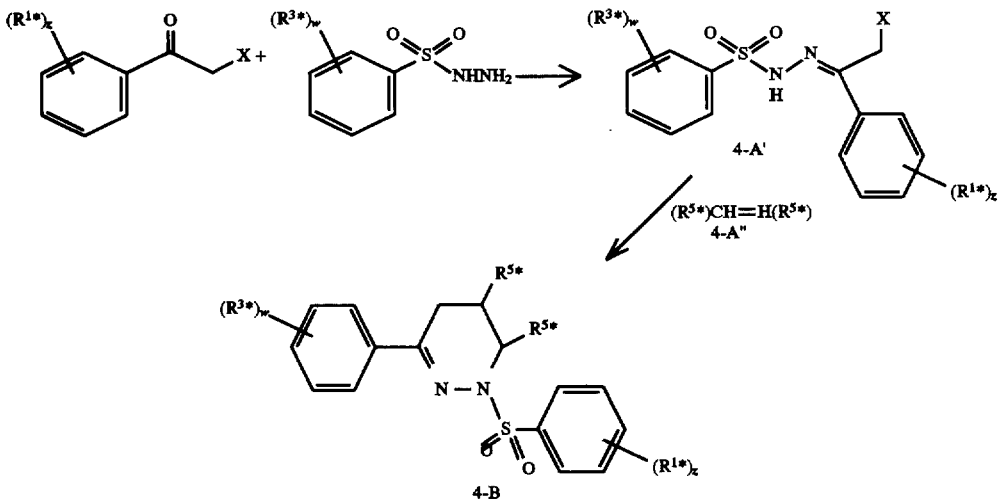

sulfate; acetates such as acetic acid; etc. Suitable base salts or alkali metal salts may be formed upon the combination of carboxy containing substituents with nitrogen containing bases, such as, dimethylamine; alkali metal containing bases, such as sodium hydroxide, lithium hydroxide, or potassium carbonate. Persons skilled in the art are well familiar with these salts. In the case of esters, carboxy containing substitutents may form desirable compounds as esters with methyl, ethyl, propyl, butyl, etc.

Preferred species possessing progestin agonist activity are encompassed by the compounds selected from the group consisting of: 3-(naphth-2-yl)-1-(4-iodobenzenesulphonyl)-1,4,5,6-tetrahydropyridazine; 3-(3,4-dichlorophenyl)-1-(4-trifluoromethylbenzenesulphonyl)-1,4,5,6-tetrahydropyridazine; 3-(3,4-dichlorophenyl)-1-(4-iodobenzenesulphonyl)-1,4,5,6-tetrahydropyridazine; 3-(3,4-dichlorophenyl)-1-(4-chlorobenzenesulphonyl)-1,4,5,6-tetrahydropyridazine; 3-(3,4-dichlorophenyl)-1-(2-naphthylenesulfonyl)-1,4,5,6-tetrahydropyridazine; 3-(3,4-dichlorophenyl)-1-(4-bromobenzenesulphonyl)-1,4,5,6-tetrahydropyridazine; 3-(3,4-dichlorophenyl)-1-(4-methylbenzenesulphonyl)-1,4,5,6-tetrahydropyridazine; 3-(4-chloro-3-trifluoromethylphenyl)-1-(4-trifluoromethylbenzenesulphonyl)-1,4,5,6-tetrahydropyridazine; 3-(4-chloro-3-trifluoromethylphenyl)-1-(4-bromobenzenesulphonyl)-1,4,5,6-tetrahydropyridazine; 3-(4-chloro-3-trifluoromethylphenyl)-1-(4-iodobenzenesulphonyl)-1,4,5,6-tetrahydropyridazine; (R,S) 3-(3,4-dichlorophenyl)-1-(4-iodobenzenesulphonyl)-6-methyl-1,4,5,6-tetrahydropyridazine and (R,S) 3-(4-chloro-3-trifluoromethylphenyl)-1-(4-iodobenzenesulphonyl)-6-methyl-1,4,5,6-tetrahydropyridazine.

Preferred species possessing progestin antagonist activity encompassed by the compounds selected from the group consisting of:
3-(3,4-dichlorophenyl)-1-(2,3-dichlorobenzenesulphonyl)-1,4,5,6-tetrahydropyridazine; 3-(3,4-dichlorophenyl)-1-(2,5-dichlorobenzenesulphonyl)-1,4,5,6-tetrahydropyridazine; 3-(3,4-dichlorophenyl)-1-(2-(3-carbomethoxypropxy)-5-bromobenzenesulphonyl)-1,4,5,6-tetrahydropyridazine; 3-(4-chloro-3-trifluoromethylphenyl)-1-(2,5-dichlorobenzenesulphonyl)-1,4,5,6-tetrahydropyridazine and (R,S) 3-(3,4-dichlorophenyl)-1-(2,5-dichlorobenzenesulphonyl)-5-methyl-1,4,5,6-tetrahydropyridazine.

Preferred species possessing bone growing activity encompassed by the compounds selected from the group consisting of:
1-(3,4-dichlorobenzoyl)-3-phenyl-1,4,5,6-tetrahydropyridazine; 1-(3,4-dichlorothiobenzoyl)-3-phenyl-1,4,5,6-tetrahydropyridazine; 1-(3,4-difluorothiobenzoyl)-3-phenyl-1,4,5,6-tetrahydropyridazine; 1-(3-bromo-4-fluorothiobenzoyl)-3-phenyl-1,4,5,6-1tetrahydropyridazine; (R,S)-1-(3,4-difluorobenzoyl)-5-methyl-3-phenyl-1,4,5,6-tetrahydropyridazine; (R,S)-1-(3,4-dichlorobenzoyl)-5-methyl-3-phenyl-1,4,5,6-tetrahydropyridazine; (R,S)-1-(3,4-dichlorothiobenzoyl)-5-methyl-3-phenyl-1,4,5,6-tetrahydropyridazine; (R,S)-1-(3,4-difluorothiobenzoyl)-5-methyl-3-phenyl-1,4,5,6-tetrahydropyridazine
1-(3,4-dichlorobenzoyl)-3-(thien-2-yl)-1,4,5,6-tetrahydropyridazine; 1-(3,4-dichlorobenzoyl)-3-(thien-3-yl)-1,4,5,6-tetrahydropyridazine; 1-(3,4-dichlorothiobenzoyl)-3-(thien-2-yl)-1,4,5,6-tetrahydropyridazine and 1-(3,4-dichlorothiobenzoyl)-3-(thien-3-yl)-1,4,5,6-tetrahydropyridazine.

Certain compounds of the invention exhibit in vivo activity and they are useful in treating biological disorders and conditions that are modulated agonistically or antagonistically by steroids, e.g., contraception, menopause, endometriosis, breast cancer, cycle synchrony, uterine fibroids, cervical dilation, osteoporosis and central nervous system conditions.

Pharmaceutical compositions that are used in treating the biological disorders or conditions comprise the compounds of the invention as the active ingredients in intimate admixture with a pharmaceutical carrier can be prepared according to conventional pharmaceutical compounding techniques. The carrier may take a wide variety of forms depending on the form of preparation desired for administration, e.g., intravenous, oral, transdermal, intravaginal, suppository or parenteral. The composition may also be administered by means of an aerosol. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included, injectable suspensions may also be prepared, in which case appropriate liquid carriers, suspending agents and the like may be employed. The pharmaceutical compositions will generally be in the form of a dosage unit, e.g., tablet, capsule, powder, injection, teaspoonful and the like, from about 1 µg/kg to about 100 mg/kg, and preferably from about 20 µg/kg to about 20 mg/kg of the active ingredients.

Therefore, the compounds may be useful as contraceptives, and in the treatment of menopause, endometriosis, breast cancer, cycle synchrony, uterine fibroids, cervical dilation and osteoporosis.

The following experimental examples describe the invention in greater particularity and are intended to be a way of illustrating but not limiting the invention.

EXAMPLES

6-(4-Chlorophenyl)pyridazin-3-one

Hydrazine (8.9 mL, 0.28 mol) was added to a suspension of 3-(4-chlorobenzoyl)propionic acid (30.0 g, 0.14 mol) in EtOH. The resulting mixture was heated to reflux for 1 hour, stirred at room temperature overnight and chilled with an ice bath. The title compound precipitated out of this mixture (23.85 g, 81%) as a yellow solid: mp 175°–176° C.

The following pyridazin-3-ones listed in Table 1 were prepared essentially by the above procedure, using the appropriate starting materials.

TABLE 1

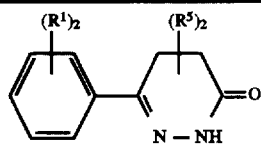

| Cpd | R¹ | R⁵ | mp |
|---|---|---|---|
| 1-1 | 4-Cl | H | 175–176 |
| 1-2 | 3-Cl | H | 148–150 |
| 1-3 | 4-Br | H | 165–166 |
| 1-4 | H | H | 192–194 |
| 1-5 | 4-NMe$_2$ | H | |
| 1-6 | 4-OMe | H | 148–149 |
| 1-7 | H | H | 150–151 |
| 1-8 | 3-Cl, 4-Cl | H | 168–169 |
| 1-9 | 3-CF$_3$, 4-Cl | H | 191–192 |
| 1-10 | 4-n-Bu | H | |
| 1-11 | 3-Br, 4-NH$_2$ | H | |
| 1-12 | 3-Br, 5-Br | H | |
| 1-13 | 3,4-(CH$_2$)$_4$— | H | |
| 1-14 | 3,4-O(CH$_2$)$_2$O— | H | |
| 1-15 | 3,4-CH=CHCH=CH— | H | 209–210 |
| 1-16 | 2,3-CH=CHCH=CH— | H | 135–136 |
| 1-17 | 3,4-N(Me)C(O)CH$_2$S(O)$_2$— | H | 300–301 |
| 1-18 | 3,4-N(Me)C(O)CH$_2$S— | H | 241–242 |
| 1-19 | 4-SCH$_3$ | H | |
| 1-20 | 4-SO$_2$CH$_3$ | H | |
| 1-21 | H | 5-CH$_3$ | 155–158 |
| 1-22 | H | 5-CH$_3$, 5-CH$_3$ | 166–167 |
| 1-23 | 4-Ph | H | 295–300 |

TABLE 2

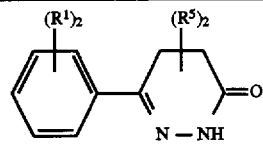

| Cpd | R¹ | R⁵ |
|---|---|---|
| 2-1 | 4-Cl | H |
| 2-2 | 3-Cl | H |
| 2-3 | H | H |
| 2-4 | 4-NHMe$_2$ | H |
| 2-5 | 4-OMe | H |
| 2-6 | H | H |
| 2-7 | H | 5-CH$_3$ |
| 2-8 | H | 5-CH$_3$, 5-CH$_3$ |
| 2-9 | 3-Cl, 4-Cl | H |
| 2-10 | 3-CF$_3$, 4-Cl | H |
| 2-11 | 4-n-Bu | H |
| 2-12 | 3-Br, 4-NH$_2$ | H |
| 2-13 | 3-Br, 5-Br | H |
| 2-14 | 3,4-CH=CHCH=CH— | H |
| 2-15 | 3,4-O(CH$_2$)$_2$O— | H |
| 2-16 | 3,4-CH=CHCH=CH— | H |
| 2-17 | 3,4-N(Me)C(O)CH$_2$S— | H |
| 2-18 | 3,4-N(Me)C(O)CH$_2$S(O)$_2$— | H |
| 2-19 | 4-SCH$_3$ | H |
| 2-20 | 4-SO$_2$CH$_3$ | H |
| 2-21 | 4-Ph | H |

Example 2

(4-Chlorophenyl)pyridazine

A lithium aluminum hydride/THF solution (1 Molar, 173 mL) was added dropwise to a suspension of pyridazin-3-one 1B (R$_1$=4-Cl; 12.0 g, 57.5 mmol) in THF at 0° C. The resulting mixture was heated to reflux for 1 hour, and cooled to 0° C. Water (6.5 mL) was added to this mixture, followed by the successive addition of NaOH (1N, 6.5 mL), and of water (12 mL). The resulting precipitate was removed from the mother liquor followed by the treatment of said mother liquor with potassium carbonate. The resulting organic solution was concentrated arylphosphonyl dihalide to give the title compound as a thick oil (9.65 g, 87%).

The following pyridazines listed in Table 2 were prepared essentially by the above procedure, using the appropriate starting materials. All of the products are oils.

Example 3

3-(4-Chloro-3-trifluoromethylphenyl)-1-(4-iodobenzenesulfonyl)-1,4,5,6-tetrahydropyridazine (Compound 1)

4-iodobenzenesulfonyl chloride (1.18 g, 5.03 mmol) was added at room temperature to a solution of pyridazine (1C) (R$_1$=3-CF$_3$, 4-Cl: 0.62 g, 2.36 mmol) in pyridine and the resulting mixture was stirred for 16 h. 2N HCl was added to the reaction mixture followed by successive washes with methylene chloride. The combined organic extracts were dried (K$_2$CO$_3$), concentrated arylphosphonyl dihalide and passed through a column of silica gel. The desired fractions were recrystallized from ethyl acetate/ether to give the title compound as a solid (0.30 g): mp 153°–154° C.

Anal. Calc'd for C$_{17}$H$_{13}$ClF$_3$IN$_2$O$_2$S: C, 38.61; H, 2.48; N, 5.30 Found: C, 38.81; H, 2.44; N, 5.32

The following acylated pyridazines listed in Table 3, Table 3a and Table 4 were prepared essentially by the above procedure, using the appropriate starting materials.

TABLE 3

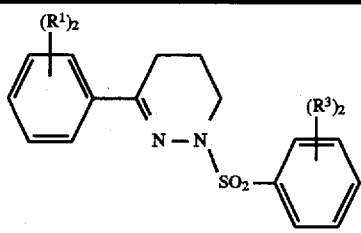

| Cpd | R¹ | R³ | mp:(°C.) | C | H | N |
|---|---|---|---|---|---|---|
| 1 | 3-$CF_3$, 4-Cl | 4-I | 153–154 | 38.81 | 2.44 | 5.32 |
| 2 | H | 4-Me | 160–161 | 65.00 | 5.72 | 9.05 |
| 3 | 4-OMe | 4-Me | 141–142 | 62.50 | 5.69 | 8.13 |
| 4 | 4-Cl | 4-$NO_2$ | 164–165 | 50.73 | 3.58 | 11.15 |
| 5 | 4-Cl | 2-Cl, 5-Cl | 148–149 | 47.67 | 3.16 | 6.91 |
| 6 | 4-Cl | 4-Cl | 170–171 | 52.14 | 3.68 | 7.52 |
| 7 | 4-F | 4-Cl | 151–152 | 54.31 | 3.84 | 8.08 |
| 8 | 4-Cl | 4-Me | 157–158 | 58.57 | 4.86 | 8.01 |
| 9 | 4-F | 4-Me | 139–140 | 61.42 | 4.96 | 8.45 |
| 10 | 4-F | 4-$NO_2$ | 152–153 | 52.78 | 3.69 | 11.34 |
| 11 | 4-F | 2-Cl, 5-Cl | 122–123 | 49.50 | 3.14 | 7.16 |
| 12 | 4-Cl, 3-Cl | 4-Cl | 153–154 | 48.61 | 3.23 | 7.16 |
| 13 | 4-Cl | 4-Br | 178–180 | 46.50 | 3.18 | 6.56 |
| 14 | 4-Cl | 3-$NO_2$ | 162–163 | 50.66 | 3.51 | 10.86 |
| 15 | 4-Cl | 2,3-CH=CHCH=CH— | 148–149 | 62.62 | 4.07 | 7.27 |
| 16 | 4-Cl | 4-I | 162–163 | 41.93 | 2.80 | 5.98 |
| 17 | 4-Cl | 4-F | 159–160 | 54.57 | 3.77 | 8.07 |
| 18 | 4-F | 4-F | 147–148 | 57.18 | 3.87 | 8.55 |
| 19 | 4-F | 4-Br | 157–158 | 48.34 | 3.23 | 6.87 |
| 20 | 4-F | 4-I | 150–151 | 43.27 | 2.90 | 6.04 |
| 21 | 4-F | 4-F, 3-$NO_2$ | 149–150 | 52.88 | 3.60 | 11.37 |
| 22 | 4-Cl, 3-Cl | 2-Cl, 5-Cl | 176–177 | 43.88 | 2.68 | 6.22 |
| 23 | 4-F | 2-$NO_2$, 4-$NO_2$ | 149–150 | 46.85 | 3.11 | 13.71 |
| 24 | 4-F | 2-$NO_2$ | 159–160 | 52.48 | 3.76 | 11.44 |
| 25 | 4-F | 3,4-CH=CHCH=CH— | 179–180 | 65.14 | 4.63 | 7.64 |
| 26 | 4-F | 2-$CO_2$Me | 150–151 | 57.22 | 4.51 | 7.40 |
| 27 | 4-Cl | 2-$NO_2$ | 182–183 | 50.68 | 3.74 | 11.34 |
| 28 | 4-Cl | 2-$NO_2$, 4-$NO_2$ | 186–187 | 45.22 | 2.97 | 13.20 |
| 29 | 4-Cl | 2-$CO_2$Me | 153–154 | 55.15 | 4.22 | 7.12 |
| 30 | 4-Cl | 3-Cl, 4-Cl | 163–164 | 47.63 | 3.18 | 7.08 |
| 31 | 4-Cl | 3-Cl, 5-Cl | 149–150 | 47.70 | 3.14 | 6.93 |
| 32 | 4-Cl | 2-F, 4-F | 115–116 | 52.11 | 3.46 | 7.51 |
| 33 | 4-Cl | 3-$CF_3$, 5-$CF_3$ | 154–155 | 45.99 | 2.66 | 5.75 |
| 34 | 4-Cl | 3-$NO_2$ | 187–188 | 46.24 | 3.12 | 10.10 |
| 35 | 4-Cl | 3-$CF_3$ | 178–179 | 50.76 | 3.47 | 6.93 |
| 36 | 4-Cl | 4-$CF_3$ | 126–127 | 50.97 | 3.38 | 6.90 |
| 37 | 4-Cl | H | 203–204 | 57.38 | 4.37 | 8.35 |
| 38 | 4-Cl, 3-Cl | 4-$NO_2$ | 174–175 | 46.54 | 3.14 | 10.18 |
| 39 | 4-Cl, 3-Cl | 4-Br | 175–176 | 42.42 | 2.99 | 6.43 |
| 40 | 4-Cl, 3-Cl | 4-I | 184–185 | 39.24 | 2.67 | 5.76 |
| 41 | 4-Cl, 3-Cl | 4-Me | 150–151 | 53.65 | 4.17 | 7.29 |
| 42 | 4-Cl, 3-Cl | 3,4-CH=CHCH=CH— | 136–137 | 57.49 | 3.79 | 6.74 |
| 43 | 4-Cl, 3-Cl | H | 160–161 | 52.00 | 3.88 | 7.75 |
| 44 | 4-Cl | 2,3-CH=CHCH=CH— | 195–196 | 62.35 | 4.39 | 7.30 |
| 45 | 4-Cl, 3-Cl | 4-n-Bu | 140–141 | 61.39 | 5.90 | 7.21 |
| 46 | 4-Cl, 3-Cl | 3,4-C($NMe_2$)=CHCH=CH— | 164–165 | 61.80 | 5.36 | 9.89 |
| 47 | 4-Cl, 3-Cl | 2-$CO_2$Me | 121–122 | 50.63 | 3.75 | 6.49 |
| 48 | H | 4-Cl | 153–154 | 57.24 | 4.34 | 8.66 |
| 49 | H | 4-Br | 145–146 | 50.65 | 3.64 | 7.68 |
| 50 | H | 4-I | 143–144 | 44.99 | 3.15 | 6.70 |
| 51 | H | 3,4-CH=CHCH=CH— | 137–138 | 68.37 | 5.19 | 8.28 |
| 52 | H | 2-Cl, 5-Cl | 140–141 | 51.93 | 3.59 | 7.16 |
| 53 | H | 4-$NO_2$ | 170–171 | 55.88 | 3.97 | 11.77 |
| 54 | H | 4-F | 125–126 | 60.54 | 4.45 | 8.39 |
| 55 | H | 4-n-Bu | 84–85 | 67.34 | 6.46 | 7.52 |
| 56 | H | 2,3-CH=CHCH=CH— | 177–178 | 68.23 | 5.10 | 7.91 |
| 57 | H | 3,4-C($NMe_2$)=CHCH=CH— | 139–140 | 67.04 | 5.66 | 10.39 |
| 58 | H | 4-Cl, 3-$NO_2$ | 127–128 | 50.50 | 3.45 | 10.98 |
| 59 | H | 2-F, 4-F | 120–121 | 56.97 | 3.84 | 8.30 |
| 60 | H | 3-Cl, 4-Cl | 140–141 | 51.99 | 3.54 | 7.55 |
| 61 | H | 4-$CF_3$ | 155–156 | 55.77 | 3.94 | 7.67 |
| 62 | H | 3-$NO_2$ | 173–174 | 55.61 | 3.99 | 11.90 |
| 63 | 4-OMe | 4-Cl | 164–165 | 56.11 | 4.47 | 7.61 |
| 64 | 4-OMe | H | 185–186 | 61.85 | 5.22 | 8.45 |

TABLE 3-continued

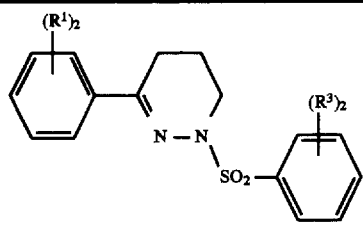

| Cpd | R¹ | R³ | mp:(°C.) | C | H | N |
|---|---|---|---|---|---|---|
| 65 | 4-OMe | 3,4-CH=CHCH=CH— | 145–147 | 66.28 | 5.22 | 7.40 |
| 66 | H | H | 167–168 | 64.04 | 5.29 | 9.32 |
| 67 | 4-Cl | 4-Cl, 4-NO₂ | 186–187 | 46.51 | 3.31 | 10.22 |
| 69 | 4-n-Bu | 2-Cl, 5-Cl | 95–97 | 56.41 | 5.22 | 6.59 |
| 70 | 4-n-Bu | 3-NO₂ | 119–120 | 59.91 | 5.61 | 10.31 |
| 71 | 4-n-Bu | 4-I | 121–122 | 49.65 | 4.69 | 5.63 |
| 72 | 4-n-Bu | 3,4-CH=CHCH=CH— | 140–141 | 70.87 | 6.33 | 6.74 |
| 73 | 4-n-Bu | 4-Cl | 108–109 | 61.32 | 5.74 | 7.04 |
| 74 | 4-n-Bu | 4-Me | 106–107 | 68.10 | 7.01 | 7.58 |
| 75 | 4-n-Bu | 4-n-Bu | 102–103 | 69.66 | 7.79 | 6.83 |
| 76 | 4-n-Bu | H | 109–110 | 67.24 | 6.71 | 7.93 |
| 77 | 3-CF₃, 4-Cl | 4-Cl | 134–135 | 46.78 | 2.91 | 6.47 |
| 78 | 3-CF₃, 4-Cl | 3,4-(CH₂)₄- | 130–131 | 38.81 | 2.44 | 5.32 |
| 79 | 3-CF₃, 4-Cl | 2-Cl, 5-Cl | 160–161 | 55.56 | 3.44 | 6.26 |
| 80 | 3-CF₃, 4-Cl | 3-Cl, 5-Cl | 124–125 | 43.42 | 2.54 | 6.02 |
| 81 | 3-CF₃, 4-Cl | 3-Cl, 4-Cl | 138–139 | 43.27 | 2.52 | 5.87 |
| 82 | 3-CF₃, 4-Cl | 4-Me | 136–137 | 43.77 | 2.55 | 6.10 |
| 83 | 3-CF₃, 4-Cl | H | 155–156 | 52.21 | 3.73 | 6.80 |
| 84 | 4-Ph | 4-Cl | 194–195 | 64.08 | 4.62 | 6.78 |
| 85 | 4-Ph | 3,4-CH=CHCH=CH— | 193–194 | 73.28 | 5.07 | 6.52 |
| 86 | 4-Ph | H | 204–205 | 69.92 | 5.34 | 7.42 |
| 87 | 3,4-(CH₂)₄- | 4-Me | 143–144 | 68.43 | 6.81 | 7.46 |
| 88 | 3,4-(CH₂)₄- | 4-Cl | 165–166 | 61.72 | 5.57 | 7.11 |
| 89 | 3,4-(CH₂)₄- | 2-Cl, 5-Cl | 153–153 | 56.75 | 4.60 | 6.56 |
| 90 | 3,4-(CH₂)₄- | H | 151–153 | 67.52 | 6.37 | 7.91 |
| 91 | 3-Cl | 2-Cl, 5-Cl | 115–116 | 47.64 | 3.01 | 6.82 |
| 92 | 3-Cl | 4-Me | 129–130 | 58.53 | 4.91 | 8.07 |
| 93 | 3-Cl | 4-Cl | 123–124 | 51.95 | 3.66 | 7.53 |
| 94 | 3-Cl | 3,4-CH=CHCH=CH— | 154–155 | 51.95 | 3.66 | 7.53 |
| 95 | 3-Cl | H | 129–130 | 57.22 | 4.37 | 8.36 |
| 96 | 3-Cl | 4-I | 131–132 | 41.75 | 2.98 | 6.04 |
| 97 | 4-Cl, 3-Cl | 4-CF₃ | 139–141 | 46.48 | 2.92 | 6.46 |
| 98 | 4-Cl, 3-Cl | 3-CF₃ | 185–186 | 46.64 | 2.76 | 6.18 |
| 99 | 4-Br | 4-Cl | 182–183 | 46.13 | 3.18 | 6.38 |
| 100 | 4-Br | 4-Br | 192–193 | 41.80 | 2.96 | 5.73 |
| 101 | 4-Br | 4-Me | 175–176 | 51.94 | 4.29 | 6.90 |
| 102 | 4-Br | 2-Cl, 5-Cl | 168–169 | 42.56 | 2.86 | 5.99 |
| 103 | 4-Br | H | 205–206 | 50.59 | 3.92 | 7.09 |
| 104 | 4-Cl, 3-Cl | 3-Cl, 5-Cl | 142–143 | 43.76 | 2.59 | 6.10 |
| 105 | 4-Cl, 3-Cl | 2-Cl, 3-Cl | 142–144 | 43.81 | 2.66 | 6.25 |
| 106 | 4-Cl, 3-Cl | 4-F | 141–142 | 49.52 | 3.30 | 7.03 |
| 108 | 4-Cl, 3-Cl | 4-n-Bu | 128–129 | 56.43 | 5.18 | 6.28 |
| 109 | 4-Cl, 3-Cl | 3-Cl | 189–190 | 47.49 | 3.23 | 6.62 |
| 110 | 4-Cl, 3-Cl | 2,3-CH=CHCH=CH— | 150–151 | 57.16 | 3.81 | 6.46 |
| 111 | 4-Cl, 3-Cl | 3-NO₂, 4-Cl | 157–158 | 42.93 | 2.60 | 8.98 |
| 112 | 3,4-C(OMe)H=CHCH=CH— | 4-I | 143–145 | 50.19 | 3.68 | 5.37 |
| 113 | 3,4-(CH₂)₄- | 4-I | 170–172 | 50.03 | 4.47 | 5.86 |
| 114 | 4-Cl, 3-Cl | 3,4-(CH₂)₄- | 135–136 | 56.59 | 4.53 | 6.55 |
| 115 | 3-CF₃, 4-Cl | 4-Br | 139–140 | 42.45 | 2.70 | 5.82 |
| 116 | 3-CF₃, 4-Cl | 4-n-Bu | 95–96 | 54.97 | 4.79 | 6.04 |
| 117 | 3,4-CH=CHCH=CH— | 4-Cl | 160–161 | 62.38 | 4.30 | 7.24 |
| 118 | 3,4-CH=CHCH=CH— | 2-Cl, 5-Cl | 158–159 | 57.26 | 3.72 | 6.69 |
| 119 | 3,4-CH=CHCH=CH— | 4-I | 169–170 | 50.27 | 3.48 | 5.67 |
| 120 | 3,4-CH=CHCH=CH— | 4-Me | 153–154 | 69.27 | 5.26 | 7.73 |
| 121 | 4-Cl, 3-Cl | 4-n-Hex | 96–97 | 58.17 | 5.63 | 6.10 |
| 122 | 2,3-CH=CHCH=CH— | 4-Me | 159–163 | 61.99 | 4.25 | 7.09 |
| 123 | 3,4-O(CH₂)₂O- | 2-Cl, 5-Cl | 147–148 | 50.61 | 3.53 | 6.56 |
| 124 | 3,4-O(CH₂)₂O- | 4-Cl | 143–145 | 55.21 | 4.04 | 7.17 |
| 125 | 3-CF₃, 4-Cl | 4-CF₃ | 104–106 | 46.30 | 2.54 | 2.65 |
| 126 | 3-CF₃, 4-Cl | 3-CF₃ | 144–145 | 45.88 | 2.72 | 5.84 |
| 127 | 3-CF₃, 4-Cl | 3-NO₂ | 149–150 | 45.58 | 2.82 | 9.19 |
| 128 | 3-CF₃, 4-Cl | 4-NO₂ | 172–173 | 45.66 | 2.81 | 8.98 |
| 129 | 3,4-CH=CHCH=CH— | 4-CF₃ | 166–167 | 60.08 | 3.74 | 6.67 |
| 130 | 3,4-CH=CHCH=CH— | 3-CF₃ | 154–155 | 60.14 | 3.79 | 6.66 |

TABLE 3-continued

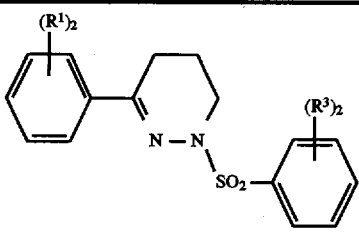

| Cpd | R¹ | R³ | mp:(°C.) | C | H | N |
|---|---|---|---|---|---|---|
| 131 | 3,4-CH=CHCH=CH— | H | 198–200 | 68.39 | 5.01 | 8.00 |
| 132 | 3,4-CH=CHCH=CH— | 3,4-CH=CHCH=CH— | 173–174 | 71.63 | 4.67 | 6.91 |
| 133 | H | 4-OCH₃ | 115–117 | 61.89 | 5.41 | 8.15 |
| 134 | 4-SCH₃ | 4-CH₃ | 159–161 | 60.02 | 5.56 | 7.74 |
| 135 | 4-SCH₃ | 4-I | 177–179 | 43.39 | 3.57 | 5.84 |
| 136 | 4-Cl, 3-Cl | 2-O(CH₂)₃CO₂Me, 5-Br | 76–79 | 45.66 | 4.06 | 4.61 |
| 137 | 4-OMe | 2-O(CH₂)₃CO₂Me, 5-Br | 96–97 | 51.20 | 5.01 | 5.12 |
| 138 | 3,4-N(Me)C(O)CH₂S— | 4-I | 199–203 | 43.62 | 3.09 | 7.65 |
| 139 | 3,4-N(Me)C(O)CH₂S— | 4-I | 127–131 | 39.97 | 3.01 | 7.02 |
| 140 | H | 4-SCH₃ | 120–121 | 58.89 | 5.26 | 7.99 |

TABLE 3a

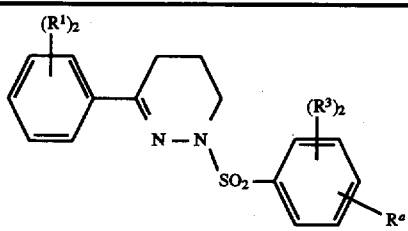

| Cpd | R¹ | R³ | Rᵃ | mp:(°C.) | C | H | N |
|---|---|---|---|---|---|---|---|
| 68 | 4-Cl | 2-Cl, 4-Cl | 5-Cl | 151–152 | 43.87 | 2.83 | 6.42 |
| 107 | 4-Cl, 3-Cl | 2-Cl, 4-Cl | 5-Cl | 184–185 | 40.60 | 2.34 | 5.85 |

TABLE 4

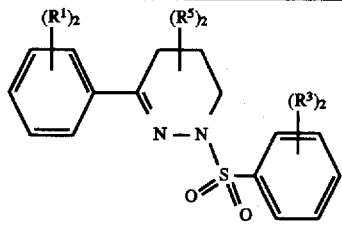

| Cpd | R¹ | R³ | R⁵ | mp:(°C.) | C | H | N |
|---|---|---|---|---|---|---|---|
| 141 | H | 3-CF₃ | 5-Me | 30–131 | 56.37 | 4.14 | 7.32 |
| 142 | H | 4-Br | 5-Me | 34–135 | 52.00 | 4.26 | 7.11 |
| 143 | H | 4-Me | 5-Me | 38–139 | 65.55 | 6.24 | 8.48 |
| 144 | H | 2-Cl, 5-Cl | 5-Me | 54–155 | 53.25 | 4.00 | 7.24 |

Example 4

3-(Dibenzofuran-3-yl)-1-(4-iodobenzenesulfonyl)-1,4,5,6-tetrahydropyradazine (Compound 145)

4-Iodobenzenesulfonyl chloride (0.54 g, 2.16 mmol) was added at room temperature to a solution of 4-oxo-4-(dibenzofuran-4-yl)butyric acid (0.65 g, 2.16 mmol) in pyridine and the resulting mixture was stirred for 16 hours. 2N HCl was added to the reaction mixture followed by successive washes with methylene chloride. The combined organic extracts were dried (K₂CO₃), concentrated arylphosphonyl dihalide and passed through a column of silica gel. The desired fractions were recrystallized from ethyl acetate/ether/hexane to give the title compound as a solid (0.14 g): mp 166°–169° C.

Anal. Calc'd for C₂₂H₁₇IN₂O₃S: C, 51.17; H, 3.32; N, 5.43 Found: C, 51.27; H, 3.30; N, 5.23

Example 5

1-(4-Methylbenzoyl)-3-(4-chlorophenyl)-1,4,5,6-tetrahydropyridazine (Compound 146)

The title compound was prepared as described in Example 4 starting with 4-oxo-4-(dibenzofuran-4-yl)butyric acid (0.54 g, 2.16 mmol) and 4-chlorobenzenesulfonyl chloride (0.46 mL, 2.16 mmol) to give a solid: mp 163°–166° C.

Anal. Calc'd for C₂₂H₁₇ClN₂O₃S: C, 69.10; H, 5.49; N, 8.95 Found: C, 69.31; H, 5.35; N, 9.02

Example 6

1-(4-Methylsulfinylbenzenesulfonyl)-3-phenyl-1,4,5,6-tetrahydropyridazine (Compound 147l)

MCPBA (0.63 g) was added at room temperature to a solution of 3-phenyl-1-(4-thiomethylbenzenesulfonyl)-1,4,5,6-tetrahydropyridazine (1.0 g) in methylene chloride. The resulting mixture was stirred and monitored by TLC until the starting pyridazine was exhausted. The mixture was concentrated arylphosphonyl dihalide and purified by column chromatography on silica gel using methylene chloride as an eluent to give a solid: mp 137°–139° C.

Anal. Calc'd for C₁₇H₁₈N₂O₃S2: C, 56.33; H, 5.00; N, 7.73 Found: C, 56.37; H, 4.87; N, 7.54

Example 7

1-(4-Iodobenzenesulfonyl)-3-(4-methylsulfinylphenyl)-1,4,5,6-tetrahydropyridazine (Compound 148)

A solution of 1-(4Iodobenzenesulfonyl)-3-(4-methylthiophenyl)-1,4,5,6-tetrahydropyridazine (1.27 g, 2.69 mmol) in methanol (450 mL) was added to a solution of sodium periodate (0.61 g, 2.82 mmol) in water (6 mL) and stirred at a low heat for 16 hours. The resulting mixture was filtered, concentrated arylphosphonyl dihalide and purified by column chromatography on silica gel using ether/ methylene chloride as an eluent to give the title compound as a solid: mp 191°–193° C.

Anal. Calc'd for $C_{17}H_{17}IN_2O_3S_2$: C, 41.81; H, 3.52; N, 5.73 Found: C, 42.21; H, 3.77; N, 5.46

Example 8

1-(4-Methylnenzenesulfonyl)-3-(4-methylsulfinylphenyl)-1,4,5,6-tetrahydropyridazine (Compound 149)

The title compound was prepared as described in Example 7 starting with 1,4,5,6-tetrahydro-1-(4-methylbenzenesulfonyl)-3-(4-methylthiophenyl)pyridazine (1.0 g, 2.77 mmol) and sodium periodate (0.62 g, 2.91 mmol) in water (5.82 mL) to give a solid: mp 212°–213° C.

Anal. Calc'd for $C_{18}H_{20}N_2O_3S_2$: C, 57.42; H, 5.37; N, 7.44 Found: C, 57.32; H, 5.45; N, 7.52

Example 9

1-(Methylbenzenesulfonyl)-3-(4-methylsulfonylphenyl)-1,4,5,6-tetrahydropyridazine (Compound 150)

The title compound was prepared as described in Example 6 staring with 1-(4-methylbenzenesulfonyl)-3-(4-methylsulfinylphenyl)-1,4,5,6-tetrahydropyridazine (0.5 g, 1.33 mmol) and MCPBA (0.28 g, 1.33 mmol) to give a solid: mp 229°–230° C.

Anal. Calc'd for $C_{18}H_{20}N_2O_4S_2$: C, 55.08; H, 5.15; N, 7.13 Found: C, 54.73; H, 5.28; N, 6.82

Example 10

1-(4-Iodobenzenesulfonyl)-3-(4-methylsulfonylphenyl)-1,4,5,6-tetrahydropyridazine (Compound 151)

The title compound was prepared as described in Example 6 staring with 1-(4-iodobenzenesulfonyl)-3-(4-methylsulfinylphenyl)-1,4,5,6-tetrahyclropyridazine (0.5 g, 1.02 mmol) and MCPBA (0.22 g, 1.02 mmol) to give a solid: mp 198°–204° C.

Anal. Calc'd for $C_{18}H_{20}IN_2O_4S_2$: C, 40.48; H, 3.40; N, 5.55 Found: C, 40.45; H, 3.07; N, 5.44

Example 11

3-(4-Fluorophenyl)-1-(pentafluorobenzenesulfonyl)-1,4,5,6-tetrahydropyridazine (Compound 152)

The title compound was prepared as described in Example 3 starting with pyridazine (1C) ($R_1$=4-F) and pentafluorobenzenesulfonyl chloride to give a solid: mp 140°–141° C.

Anal. Calc'd for $C_{16}H_{10}F_6N_2O_2S$: C, 47.06; H, 2.47; N, 686 Found: C, 47.14; H, 2.32; N, 6.85

Example 12

1-(4-Aminobenzenesulfonyl)-3-(4-chlorophenyl)-1,4,5,6-tetrahydropyridazine (Compound 153)

(4-Chlorophenyl)-1-(4-nitrobenzenesulfonyl)-1,4,5,6-tetrahydropyridazine (2.12 g, 5.60 mmol) was suspended in acetic acid at 80° C. Iron filings (3.0 g) were added to this suspension and the resulting reaction mixture was heated at 80° C. for 30 minutes and filtered. Upon cooling the title compound precipitated out of this mixture as a solid: mp 205°–206° C.

Anal. Calc'd for $C_{16}H_{16}ClN_3O_2S$: C, 54.92; H, 4.61; N, 12.01 Found: C, 54.92; H, 4.64; N, 12.17

Example 13

1-(4-Aminoacetylbenzenesulfonyl)-3-(4-chlorophenyl)-1,4,5,6-tetrahydropyridazine (Compound 154)

(4-Aminobenzenesulfonyl)-3-(4-chlorophenyl)-1,4,5,6-tetrahydropyridazine (0.52 g) was dissolved in acetic anhydride and stirred at room temperature for 1.5 hours. Upon cooling the title compound precipitated out of this mixture as a solid: mp 247°–248° C.

Anal. Calc'd for $C_{18}H_{18}ClN_3O_3S$: C, 55.16; H, 4.64; N, 10.72 Found: C, 55.34; H, 4.60; N, 10.74

Example 14

3-Phenyl-1-(4-methylbenzenesulfonyl)-4,4a,5,7a-tetrahydro-1 H-cyclopenta[c]pyridazine (Compound 155)

4-Toluenesulfonylhydrazide (5 g) was added to a solution of alphachloroacetophenone (4.55 g) in ether. The mixture was heated at reflux for 2 hours and concentrated arylphosphonyl dihalide. Cooling the resulting residue to 0° C. produced a solid precipitate which was washed with hexane and dried to give the hydrazone (4A') (X=Cl, $H_1$=H, $R_3$=4-$CH_3$; 5.3 g) as a solid:

Freshly distilled cyclopentadiene (3 mL) was added to a solution of hydrazone (4A') (X=Cl, $H_1$=H, $R_3$=4-$CH_3$; 1.5 g) in THF, followed by the addition of sodium bicarbonate (2.5 g). The mixture was stirred at 22° C. for 12 hours and filtered through celite. The filtrate was concentrated arylphosphonyl dihalide, and the resulting residue was chilled with ice and triturated with ethanol. A solid precipitated out of this mixture which was collected and washed with hexane to give the title compound as a solid: mp 163°–165° C.

Anal. Calc'd for $C_{20}H_{20}N_2O_2S$: C, 68.15; H, 5.73; N, 7.94 Found: C, 67.97; H, 5.94; N, 8.26

Example 15

4,4a,5,6,7,7a-Hexahydro-3-phenyl-1-(4-methylbenzenesulfonyl)-1H-cyclopenta[c]pyridazine (Compound 156)

A catalytic amount of palladium on carbon was added to a solution of 3-phenyl-1-(4-tolylsulfonyl)-4,4a,5,7a-tetrahydro-1H-cyclopenta[c]pyridazine (0.5 g) in ethanol. The suspension was placed in a Parr Shaker apparatus under a $H_2$ atmosphere (40 PSI) and shaken for 3 hours. The mixture was filtered through celite and concentrated. The resulting residue was purified by recrystallization from ethyl acetate to give the title compound as a solid: mp 171°–176° C.

Anal. Calc'd for $C_{20}H_{22}N_2O_2S$: C, 67.76; H, 6.27; N, 7.90 Found: C, 67.63; H, 6.38; N, 7.99

Example 16

1,4,4a,9a-Tetrahydro-1-(4-methylbenzenesulfonyl)-3-phenyl-bicyclo[2.2.1]hept-7-enyl[5.6-a] cyclopenta-[1.2-e]pyridazine (Compound 157)

The title compound was prepared as described in Example 14 using dicyclopentadiene (5.5 mL) in place of cyclopentadiene to give a solid: mp 155°–159° C.

Anal. Calc'd for $C_{25}H_{26}N_2O_2S$: C, 71.73; H, 6.27; N, 6.69 Found: C, 71.75; H, 6.32 N, 6.60

Example 17

1,4,4a,9a,-Tetrahydro-4-(4-methylbenzenesulfonyl)-2-phenyl-3,4-diazafluorene Hemihydrate (Compound 158)

The title compound was prepared as described in Example 14 using indene (3.45 mL) in place of cyclopentadiene to give a solid: mp 180°–181° C.

Anal. Calc'd for $C_{24}H_{22}N_2O_2S$: C, 70.04; H, 5.40; N, 6.80 Found: C, 70.05; H, 5.56; N, 6.93

Example 18

1,4,4a,5,6,7,8,8a-Octahydro-8a-methoxy-1-(4-methyl-benzenesulfonyl)-3-phenyl-1,2-diazanapthalene (Compound 159)

The title compound was prepared as described in Example 14 using 1-methoxycyclohexene (2.7 g) in place of cyclopentadiene to give a solid: mp 112°–114° C.

Anal. Calc'd for $C_{22}H_{26}N_2O_3S$: C, 66.30; H, 6.60; N, 7.03 Found: C, 66.07; H, 6.34; N, 6.94

Example 19

3-(4-Chlorophenyl)-1-(4-iodobenzenesulfonyl)-4,4a,5,7a-tetrahydro-1H-cyclopenta[c]pyridiazine (Compound 160)

The title compound was prepared as described in Example 14 starting with 4-iodobenzenesulfonyl hydrazide (2 g), 2-bromo-4'-chloroacetophenone (1.57 g) and cyclopentadiene to give a solid: mp 198°–201° C.

Anal. Calc'd for $C_{19}H_{16}ClIN_2O_2S$: C, 45.75; H, 3.24; N, 5.61 Found: C, 45.72; H, 3.05; N, 5.46

Example 20

1,4,4a,9a-Tetrahydro-1-(4-methylbenzenesulfonyl)-3-(3bromophenyl)bicyclo[2.2.1]hept-7-enyl[5.6-a]cyclopenta[1.2-e]pyridiazine (Compound 161)

The title compound was prepared as described in Example 14 starting with 4-toluenesulfonyl hydrazide (8.8 g), 2-bromo-3'-bromoacetophenone (13.17 g) and dicyclopentadiene (8.8 mL) to give a solid: mp 159°–161° C.

Anal. Calc'd for $C_{25}H_{25}BrN_2O_2S$: C, 60.36; H, 5.08; N, 5.63 Found: C, 60.45; H, 4.95; N, 5.46

Example 21

4,4-Dibromo-3-(4-chloro-3-trifluoromethylphenyl)-1-(4-iodobenzenesulfonyl)-1,4,5,6-tetrahydropyridazine (Compound 162)

Bromine (5 g) in acetic acid (5 mL) was added to a solution of 3-(4-chloro-3-trifluoromethylphenyl)-1-(4-iodobenzenesulfonyl)-1,4,5,6-tetrahydropyridazine (1.0 g) in acetic acid (50 mL). The mixture was stirred at 25° C. for 3 hours and concentrated arylphosphonyl dihalide. The residue was recrystallized from ether to give the title compound as a solid: mp 148°–150° C.

Anal. Calc'd for $C_{17}H_{11}Br_2ClF_3IN_2O_2$: C, 29.74; H, 1.62; N, 4.08 Found: C, 30.02; H, 1.63; N, 4.00

Example 22

[2-(3-Chlorophenylethene)sulfonyl]-3-(4-chlorophenyl)-1,4,5,6-tetrahydropyridazine (Compound 163)

3-Chlorostyrenesulfonyl chloride (1.07 g, 4.5 mmol) was added at room temperature to a solution of pyridazine (1C) ($R_1$=4-Cl, 3-Cl: 0.88 g, 4.5 mmol) in pyridine and the resulting mixture was stirred for 16 hours. 2N HCl was added to the reaction mixture followed by successive washes with methylene chloride. The combined organic extracts were dried ($K_2CO_3$), concentrated arylphosphonyl dihalide and purified by column chromatography on silica gel. The desired fractions were recrystallized from ethyl acetate/ether to give the title compound as a solid:(0.33 g): mp 142°–143° C.

Anal. Calc'd for $C_{18}H_{16}Cl_2N_2O_2S$: C, 54.67; H, 4.09; N, 7.08 Found: C, 54.67; H, 4.09; N, 7.08

The following acylated pyridazines listed in Table 5 were prepared essentially by the above procedure, using the appropriate starting materials. The substituted styrene sulfonylchlorides used to prepare the desired compounds were synthesized using the procedure described in Culbertson, M. et al., *J. Chem. Soc.*(C) 992 (1968).

TABLE 5

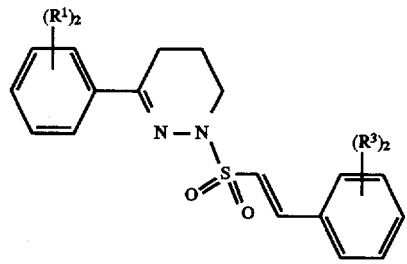

| Cpd. | $R^1$ | $R^3$ | mp:(°C.) | C | H | N |
|---|---|---|---|---|---|---|
| 164 | 4-Cl | 3,4-CH=CHCH=CH— | 167–168 | 64.36 | 4.67 | 6.83 |
| 165 | 4-Cl | 4-Cl | 161–162 | 54.59 | 3.93 | 7.13 |
| 166 | 4-Cl | H | 148–149 | 60.90 | 4.84 | 7.49 |
| 167 | 4-Cl, 3-Cl | H | 139–140 | 54.75 | 4.04 | 7.05 |

TABLE 5-continued

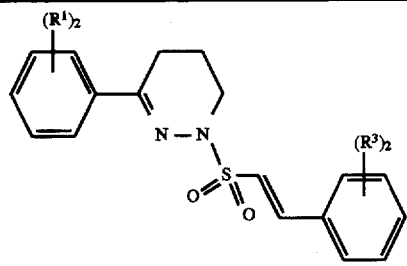

| Cpd. | R¹ | R³ | mp:(°C.) | C | H | N |
|---|---|---|---|---|---|---|
| 168 | 4-Cl, 3-Cl | Ph | 171–172 | 61.34 | 4.02 | 5.78 |
| 169 | 4-Cl, 3-Cl | 4-Me | 138–139 | 55.79 | 4.44 | 6.75 |
| 170 | 4-Cl, 3-Cl | 4-Cl | 157–158 | 50.23 | 3.54 | 6.44 |
| 171 | 4-Cl, 3-Cl | 3,4-CH=CHCH=CH— | 209–210 | 59.48 | 3.97 | 6.30 |
| 172 | 4-Cl, 3-Cl | 3-Cl | 131–132 | 50.33 | 3.35 | 6.52 |
| 173 | 4-Cl, 3-Cl | 2-Cl | 154–155 | 50.16 | 3.30 | 6.52 |
| 174 | 3,4-CH=CHCH=CH— | H | 158–159 | 70.26 | 5.01 | 7.33 |
| 175 | 3,4-CH=CHCH=CH— | 4-Me | 121–122 | 70.82 | 5.52 | 7.08 |
| 176 | 3,4-(CH$_2$)$_4$— | H | 153–155 | 69.45 | 6.54 | 7.31 |
| 177 | 3-CF$_3$, 4-Cl | 3,4-CH=CHCH=CH— | 160–161 | 57.57 | 3.79 | 5.79 |
| 178 | 3-CF$_3$, 4-Cl | 4-Cl | 167–168 | 49.08 | 3.07 | 5.93 |
| 276 | 3-CF$_3$, 4-Cl | H | 131–132 | 53.20 | 3.73 | 6.54 |

Example 23

1-Benzoyl-3-(4-chlorophenyl)-1,4,5,6-tetrahydropyridazine (Compound 179)

Benzoylchloride (1.41 mL, 12.1 mmol) was added to a solution of pyridazine (1C) (R$_1$=4-Cl: 2.36 g, 12.1 mmol) in toluene. The resulting mixture was heated to reflux for 2 hours, stirred at room temperature for 16 hours, dried and concentrated. Column chromatography on silica gel using methylene chloride as an eluent followed by recrystallization of the desired fractions from ethyl acetate gave the desired compound as a solid: mp 117°–118° C.

Anal. Calc'd for C$_{17}$H$_{15}$ClN$_2$O: C, 68.33; H, 5.07; N, 9.37 Found: C, 68.47; H, 4.86 N, 9.42

The following acylated pyridazines listed in Table 6 were prepared essentially by the above procedure, using the appropriate starting materials

TABLE 6

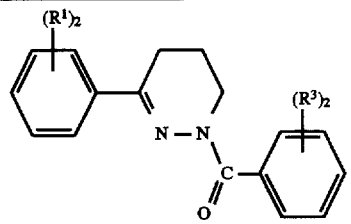

| Cpd. | R¹ | R³ | mp:(°C.) | C | H | N |
|---|---|---|---|---|---|---|
| 180 | H | 4-Me | 89–90 | 77.51 | 6.48 | 9.99 |
| 181 | 4-OMe | 4-Me | 116–117 | 74.09 | 6.72 | 8.67 |
| 182 | 4-OMe | 4-OMe | 124–125 | 70.33 | 6.36 | 8.33 |
| 183 | H | 4-OMe | 120–121 | 73.40 | 6.26 | 9.46 |
| 184 | 4-OMe | 4-Cl | 119–120 | 65.56 | 5.23 | 8.49 |
| 185 | H | 3-Cl, 4-Cl | 139–140 | 60.92 | 4.13 | 8.41 |
| 186 | H | 3-Cl | 88–89 | 68.55 | 4.90 | 9.38 |
| 187 | H | 4-Br | 139–140 | 59.44 | 4.29 | 8.11 |
| 188 | 4-OMe | 3-Cl | 102–103 | 65.91 | 5.09 | 8.58 |
| 189 | 4-OMe | 3-Cl, 4-Cl | 121–122 | 59.52 | 4.39 | 7.70 |
| 190 | 4-OMe | 4-Br | 139–140 | 57.69 | 4.47 | 7.44 |
| 191 | 4-Cl | H | 117–118 | 68.47 | 4.86 | 9.42 |
| 192 | 4-Cl | 4-Me | 130–140 | 69.31 | 5.35 | 9.02 |
| 193 | 4-Cl | 4-Cl | 156–157 | 61.44 | 4.10 | 8.46 |
| 194 | 4-Cl | OMe | 140–141 | 65.68 | 5.14 | 8.58 |
| 195 | 4-Cl | 4-t-Bu | 91–92 | 70.98 | 6.43 | 7.68 |

TABLE 6-continued

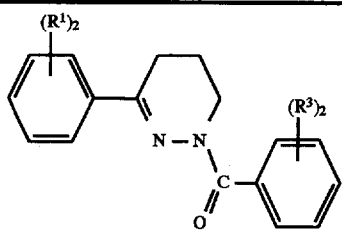

| Cpd. | R¹ | R³ | mp:(°C.) | C | H | N |
|---|---|---|---|---|---|---|
| 196 | H | H | 110–111 | 77.03 | 5.99 | 10.55 |
| 197 | H | 4-t-Bu | 92–93 | 78.61 | 7.59 | 8.68 |
| 198 | 4-Cl | 4-Br | 168–169 | 54.08 | 3.66 | 7.38 |
| 199 | 4-Cl | 3-Cl | 118–119 | 61.26 | 4.12 | 8.29 |
| 200 | 4-Cl | 3-Cl, 4-Cl | 95–96 | 55.54 | 3.34 | 7.44 |
| 201 | 4-OMe | 4-t-Bu | 123–124 | 75.45 | 7.33 | 7.87 |
| 202 | 4-Cl | 4-NO₂ | 172–174 | 59.48 | 3.96 | 11.95 |
| 203 | 4-F | 4-NO₂ | 179–180 | 62.44 | 4.29 | 12.64 |
| 204 | 4-F | 4-Cl | 126–127 | 64.33 | 4.42 | 8.83 |
| 205 | 4-F | 3-Cl, 4-Cl | 112–113 | 57.88 | 3.45 | 7.81 |
| 206 | 4-n-Bu | 3-Cl, 4-Cl | 144–145 | 49.44 | 3.05 | 6.53 |
| 207 | 4-OMe | 4-NO₂ | 153–154 | 63.75 | 4.71 | 12.36 |
| 208 | 4-OMe | 3,4-CH=CHCH=CH— | 133–134 | 76.80 | 5.63 | 8.19 |

Example 24

1-(4-Iodobenzenesulfonyl)-3-(4-dimethylaminophenyl)-1,4,5,6-tetrahydropyridazine (Compound 209)

4-Iodobenzenesulfonyl chloride (0.98 g, 3.25 mmol) was added to a solution of pyridazine (1C) ($R_1$=4-N(Me)$_2$: 0.67 g, 3.25 mmol) in pyridine. The resulting mixture was stirred at room temperature for 16 hours, dried and concentrated. The residue was purified by column chromatography on silica gel using methylene chloride as an eluent, followed by recrystallization of the desired fractions from ethyl acetate to give the desired compound as a solid: mp 203°–205° C.

Anal. Calc'd for $C_{19}H_{20}IN_3O$: C, 46.06; H, 4.30; N, 8.95 Found: C, 46.07; H, 4.18; N, 8.56

The following acylated pyridazines listed in Table 7 were prepared essentially by the above procedure, using the appropriate starting materials.

TABLE 7

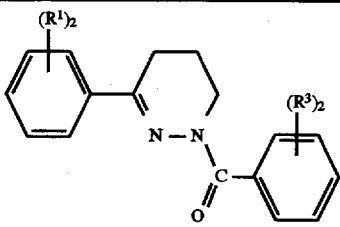

| Cpd. | R¹ | R³ | mp:(°C.) | C | H | N |
|---|---|---|---|---|---|---|
| 209 | 4-NMe₂ | 4-I | 203–205 | 46.07 | 4.18 | 8.56 |
| 210 | 4-NMe₂ | 4-F | 181–182 | 59.46 | 5.32 | 11.25 |
| 212 | 4-NMe₂ | 4-Cl | 172–174 | 66.41 | 5.72 | 12.01 |
| 213 | 4-NMe₂ | 4-Br | 188–200 | 50.88 | 4.64 | 9.56 |
| 214 | 3,4-(CH₂)₄— | 3-F, 4-F | 97–98 | 70.91 | 5.90 | 7.82 |

Example 25

1-(3-Bromo-4-fluorobenzoyl)-3-(3,4-dichlorophenyl)-1,4,5,6-tetrahydropyradazine (Compound 215)

3-Bromo-4-fluorobenzoylchloride (2.0 g, 8.42 mmol) was added to a stirred solution of pyridazine (1C) ($R_1$=3-Cl, 4-Cl: 1.93 g, 8.42 mmol) in methylene chloride at room temperature under $N_2$. Triethylamine (2.93 mL, 21.1 mmol) was added to the mixture and the progress of the reaction was monitored by TLC. The resulting mixture was concentrated arylphosphonyl dihalide and purified by column chromatography and recrystallization to give the title compound as a solid: mp 124°–126° C.

Anal. Calc'd for $C_{17}H_{12}BrCl_2FN_2O_4S$: C, 47.46; H, 2.82; N, 6.51 Found: C, 47.64; H, 2.68; N, 6.40

The following acylated pyridazines listed in Table 8 and Table 9 were prepared essentially by the above procedure, using the appropirate starting materials.

reflux under $N_2$ for 2 hours, filtered and concentrated arylphosphonyl dihalide. The resulting residue was purified by column chromatography on silica gel followed by recrystallization from ethyl acetate/ether to give the title compound (0.31 g) as a solid: mp 135°–136° C.

Anal. Calc'd for $C_{17}H_{12}Cl_2F_2N_2S$: C, 52.98; H, 3.15; N, 7.27 Found: C, 52.92; H, 2.93; N, 7.02

TABLE 8

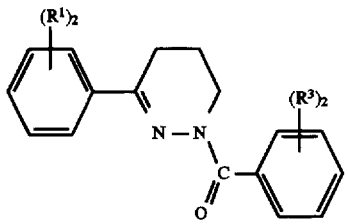

| Cpd. | $R^1$ | $R^3$ | mp:(°C.) | C | H | N |
|---|---|---|---|---|---|---|
| 216 | 3-Cl, 4-Cl | 3-Cl, 4-Cl | 118–119 | 51.03 | 2.77 | 6.84 |
| 217 | 3-Cl, 4-Cl | 4-NO₂ | 181–183 | 55.27 | 3.22 | 11.16 |
| 218 | 3-Cl, 4-Cl | 3-CF₃ | 110–112 | 53.78 | 3.17 | 6.94 |
| 219 | 3-Cl, 4-Cl | 3-Cl, 5-Cl | 149–151 | 50.70 | 2.94 | 6.77 |
| 220 | 3-Cl, 4-Cl | 4-Me | 114–115 | 62.26 | 4.48 | 7.75 |
| 221 | 3-Cl, 4-Cl | 4-t-Bu | 107–109 | 64.70 | 5.60 | 6.98 |
| 222 | 3-Cl, 4-Cl | H | 86–87 | 61.13 | 4.08 | 8.28 |
| 223 | 3-Cl, 4-Cl | 3-OMe, 4-OMe | 125–127 | 58.17 | 4.52 | 6.88 |
| 224 | 4-OMe | 3-Cl, 5-Cl | 133–134 | 59.60 | 4.47 | 7.68 |
| 225 | 3-Cl, 4-Cl | 3,4-CH=CHCH=CH– | 128–130 | 65.70 | 4.00 | 7.18 |
| 226 | 3-Cl, 4-Cl | 3-Br, 5-Br | 158–169 | 41.36 | 2.37 | 5.70 |
| 227 | H | 3-F, 4-F | 88–89 | 67.92 | 4.58 | 9.25 |
| 228 | 3-Cl, 4-Cl | 3-F, 4-F | 134–136 | 54.94 | 3.07 | 7.38 |
| 229 | H | 3-Br, 4-F | 89–90 | 56.77 | 3.77 | 7.54 |
| 230 | 3-Cl, 4-Cl | 3-Br, 4-F | 124–126 | 47.64 | 2.68 | 6.40 |
| 231 | 4-n-Bu | 3-Cl, 4-Cl | 93–94 | 64.52 | 5.52 | 6.89 |
| 232 | H | 3-Cl, 5-Cl | 101–102 | 61.18 | 4.13 | 8.25 |

TABLE 9

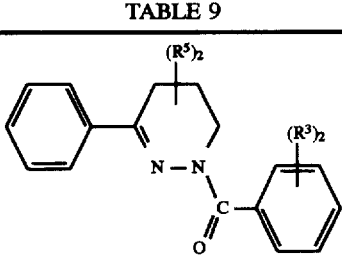

| Cpd. | $R^3$ | $R^5$ | mp:(°C.) | C | H | N |
|---|---|---|---|---|---|---|
| 233 | 3-Cl, 4-Cl | 5-Me | 124–126 | 61.91 | 4.41 | 7.86 |
| 234 | 3-Cl, 4-Cl | 5-Me, 5-Me | 108–111 | 63.16 | 4.87 | 7.53 |
| 235 | 3-F, 4-F | 5-Me | 99–100 | 68.66 | 4.87 | 8.76 |

Example 26

3-(3,4-Dichlorophenyl)-1-(3,4-difluorothiobenzoyl)-1,4,5,6-tetrahydropyridazine (Compound 236)

Phosphorous pentasulfide (1.20 g, 2.71 mmol) was added to a solution of pyridazine (3E) ($R_1$=3-Cl, 4-Cl; $R_3$=3-F, 4-F: 1.0 g, 2.71 mmol) in toluene. The mixture was heated to The following acylated pyridazines listed in Table 10 and Table 11 were prepared essentially by the above procedure, using the appropriate starting materials.

TABLE 10

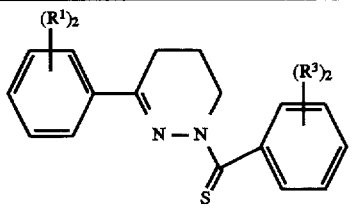

| Cpd. | $R^1$ | $R^3$ | mp:(°C.) | C | H | N |
|---|---|---|---|---|---|---|
| 237 | H | 3-Cl, 4-Cl | 151–152 | 58.32 | 3.96 | 7.96 |
| 238 | H | H | 95–98 | 72.76 | 5.65 | 9.91 |
| 239 | H | 3-F, 4-F | 134–136 | 64.44 | 4.52 | 8.74 |
| 240 | H | –OMe | 112–113 | 69.64 | 5.79 | 8.87 |
| 241 | H | 4-Me | 156–158 | 73.15 | 6.18 | 9.15 |
| 242 | 3-Cl, 4-Cl | 4-NO₂ | 189–191 | 51.72 | 3.17 | 10.40 |
| 243 | 3-Cl, 4-Cl | 3-Cl, 4-Cl | 132–133 | 48.83 | 2.73 | 6.57 |
| 244 | 3-Cl, 4-Cl | 3-Cl, 5-Cl | 134–136 | 48.92 | 2.60 | 6.42 |
| 245 | H | 3-Br, 4-F | 142–143 | 54.46 | 3.57 | 7.05 |
| 246 | 3-Cl, 4-Cl | 3-Br, 4-F | 135–138 | 46.04 | 2.47 | 5.93 |
| 247 | H | 3-Cl, 5-Cl | 132–133 | 58.42 | 3.89 | 7.73 |

TABLE 11

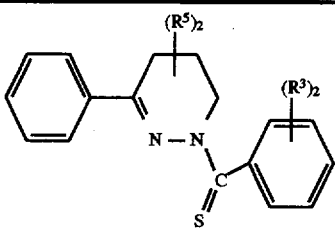

| Cpd. | R³ | R⁵ | mp:(°C.) | Analysis C | H | N |
|---|---|---|---|---|---|---|
| 248 | 3-Cl, 4-Cl | 5-Me | 128–129 | 59.55 | 4.50 | 7.65 |
| 249 | 3-Cl, 4-Cl | 5-Me, 5-Me | 142–143 | 60.58 | 4.67 | 7.46 |
| 250 | 3-F, 4-F | 5-Me | 110–112 | 65.33 | 4.87 | 8.47 |

Example 27

Methyl[3-(4-butylphenyl)-1,4,5,6-tetrahydropyridazin-1-yl]phenyl phosphonate (Compound 251)

Phenylphosphonic dichloride (0.86 mL, 6.09 mmol) was added dropwise to a solution of pyridazine 1C ($R_1$=Bu: 1.31 g, 6.09 mmol) in pyridine at 0° C. The reaction mixture was stirred at 0° C. for 1 h and warmed to room temperature. Methanol (3 mL) was added to the resulting mixture and this mixture was stirred at room temperature for 16 h. 2N HCl was added to the reaction mixture followed by successive washes with methylene chloride. The combined organic extracts were dried ($K_2CO_3$), concentrated arylphosphonyl dihalide and purified by column chromatography on silica gel; followed by recrystallization from ethyl acetate/hexane to give the title compound as a solid: (0.25 g): mp 74°–76° C.

Anal. Calc'd for $C_{21}H_{27}N_2O_2P$: C, 68.08; H, 7.36; N, 7.56 Found: C, 67.77; H, 7.20; N, 7.34

The following acylated pyridazines listed in Table 12 were prepared essentially by the above procedure, using the appropriate starting materials.

TABLE 12

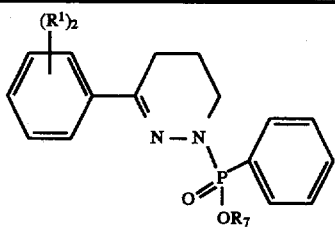

| Cpd. | R¹ | R⁷ | mp:(°C.) | Analysis C | H | N |
|---|---|---|---|---|---|---|
| 252 | H | Me | 89–91 | 64.84 | 6.00 | 8.91 |
| 253 | H | Et | 88–91 | 66.07 | 6.42 | 8.69 |
| 254 | H | i-Pr | 89–92 | 66.93 | 6.74 | 8.09 |
| 255 | 3-Cl, 4-Cl | Et | 117–119 | 54.46 | 4.84 | 6.97 |
| 256 | 3-Cl, 4-Cl | i-Pr | 103–104 | 55.45 | 5.13 | 6.67 |
| 257 | 3-Cl, 4-Cl | cyclopentyl | 115–116 | 57.67 | 5.42 | 6.34 |
| 258 | 4-F | Me | 129–131 | 61.47 | 5.26 | 8.36 |
| 259 | 4-F | Et | 111–114 | 62.51 | 5.70 | 8.39 |
| 260 | 4-Br | Me | 171–172 | 51.91 | 4.68 | 6.93 |

TABLE 12-continued

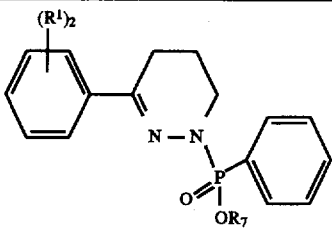

| Cpd. | R¹ | R⁷ | mp:(°C.) | Analysis C | H | N |
|---|---|---|---|---|---|---|
| 261 | 3-CF₃, 4-Cl | Me | 92–93 | 51.88 | 4.18 | 6.77 |
| 262 | 3-CF₃, 4-Cl | Et | 89–90 | 52.92 | 4.20 | 6.35 |
| 263 | 4-n-Bu | Et | <25 | 68.50 | 7.90 | 7.14 |
| 264 | 4-OMe | Me | 155–156 | 62.85 | 6.08 | 8.05 |

Example 28

6-(4-Amino-3,5-dibromophenyl)-4,5-dihydropyridazin-3-one (4-Amino-3,5-dibromphenyl)-2,3,4,5-tetrahydropyridazine was prepared as described in Example 2 starting with 6-(4-amino-3,5-dibromophenyl)-4,5-dihydropyridazin-3-one and LAH in THF to give a solid which was taken on to the next step without further purification.

The title compound was prepared as described in Example 1 starting with hydrazine and 3-(4-amino-3,5-dibromobenzoyl)propionic acid in ethanol to give a solid: mp 212°–214° C.

Example 29

(3-4-Amino-3,5-dibromophenyl)-1-(3,4-dichlorobenzoyl)-1,4,5,6-tetrahydropyridazine (Compound 265)

3-(4-Amino-3-bromophenyl)-1-(3,4-dichlorobenzoyl)-1,4,5,6-tetrahydropyridazine (Compound 266)

3,4-dichlorobenzolylchloride (2.74 g, 8.24 mmol) was added to a stirred solution of pyridazine 1-C ($R_1$=3-Cl, 4-Cl: 1.73 g, 8.42 mmol) in methylene chloride at room temperature under $N_2$. Triethylamine (3.5 mL) was added to the mixture and the resulting mixture was stirred overnight. 2N HCl was added to the reaction mixture followed by successive washes with methylene chloride. The combined organic extracts were dried ($K_2CO_3$), concentrated arylphosphonyl dihalide and passed through a column of silica gel using methylene chloride as an eluent. Column fractions containing both Compound 265 and Compound 266 were concentrated arylphosphonyl dihalide to give the title compounds as a solids: Compound 265 mp 179°–182° C.

Anal. Calc'd for $C_{17}H_{13}Br_2Cl_2N_3O$: C, 40.34; H, 2.59; N, 8.30 Found: C, 40.30; H, 2.58; N, 7.92

Compound 266 mp 202°–206° C.

Anal. Calc'd for $C_{17}H_{14}BrCl_2N_3O$: C, 47.79; H, 3.31; N, 9.83 Found: C, 47.59; H, 3.20; N, 9.41

Example 30

3-(3,5-Dibromophenyl)-1-(3,4-dichlorobenzoyl)-1,4,5,6-tetrahydropyridazine (Compound 267)

NaNO$_2$ (0.24 g, 3.43 mmol) was added to a suspension of 3-(4-amino-3,5-dibromophenyl)-1-(3,4-dichlorobenzoyl)-1,4,5,6-tetrahydropyridazine (1.0 g, 1.98 mmol, HBr (25%, 3 mL) and water (6 mL)in ethanol (50 mL). The resulting mixture was stirred and heated at a low temperature for 1.5 hours. CuBr$_2$ in HBr (48%, 6 mM) was added to the reaction mixture and the resulting mixture was stirred for 3 hours at room temperature. Water was added to the reaction and a solid precipitated from this mixture. The solid was purified by column chromatography to give the title compound as a white solid: mp 179°–182° C.

Anal. Calc'd for C$_{17}$H$_{12}$Br$_2$Cl$_2$N$_2$O: C, 41.57; H, 2.47; N, 5.70 Found: C, 41.54; H, 2.39; N, 5.42

Example 31

3-(3,4-Dichlorophenyl)-1-(2-thienoyl)-1,4,5,6-tetrahydropyridazine (Compound 268)

The title compound was prepared as described in Example 24 starting with pyridazine 1-C (R$_1$=3-Cl, 4-Cl: 1.92 g, 8.39 mmol) and 2-thienoyl chloride (1.23 g, 8.39 mmol) to give a solid (0.59 g, 21%): mp 116°–118° C.

Anal. Calc'd for C$_{15}$H$_{12}$Cl$_2$N$_2$OS: C, 53.09; H, 3.57; N, 8.25 Found: C, 53.12; H, 3.38; N, 8.23

Example 32

3-(3,4-Dichlorophenyl)-1-(2-furoyl)-1,4,5,6-tetrahydropyridazine (Compound 269)

The title compound was prepared as described in Example 24 starting with pyridazine (C) (R$_1$=3-Cl, 4-Cl: 1.63 g, 7.1 mmol) and 2-furoylchloride (0.93 g, 7.1 mmol) to give a solid (0.62 g, 27%): mp 97°–98° C.

Anal. Calc'd for C$_{15}$H$_{12}$Cl$_2$N$_2$O$_2$: C, 55.73; H, 3.75; N, 8.66 Found: C, 55.63; H, 3.79; N, 8.66

Example 33

4-Bromo-1-(3,4-dichlorobenzoyl)-3-phenyl-1,4,5,6-tetrahydropyridazine (Compound 270)

The title compound was prepared as described in Example 22 starting with 3-(3,4-difluorobenzoyl)-3-phenyl-1,4,5,6-tetrahydropyridazine and bromine to give a solid: mp 168°–169° C.

Anal. Calc'd for C$_{17}$H$_{13}$BrCl$_2$N$_2$O: C, 49.55; H, 3.18; N, 6.80 Found: C, 49.34; H, 3.16; N, 6.52

Example 34

4-Bromo-1-(3-bromo-4-fluorobenzoyl)-3-phenyl-1,4,5,6-tetrahydropyridazine (Compound 271)

The title compound was prepared as described in Example 22 starting with 1- (3-bromo-4-fluorobenzoyl)-3-phenyl-1,4,5,6-tetrahydropyridazine and bromine to give a solid: mp 147°–148° C.

Anal. Calc'd for C$_{17}$H$_{13}$Br$_2$FN$_2$O: C, 46.39 H, 2.98; N, 6.37 Found: C, 46.07; H, 2.84; N, 6.27

Example 35

3-(3,4-Dichlorophenyl)-1-(4-pentafluoroethylbenzenesulfonyl)-1,4,5,6-tetrahydropyridazine (Compound 272)

A slurry of 3-(3,4-dichlorophenyl)-1-(4-iodobenzenesulfonyl)-1,4,5,6-tetrahydropyridazine (2.28 g), copper iodide (1.8 g), sodium pentafluoropropionate (1.58 g) and DMF (20 mL) in toluene (20 mL) was distilled at 120° C., until most of the toluene was removed. The resulting mixture was heated to 155° C. for 2 hours, cooled, poured into water and extracted with methylene chloride. The combined organic extracts were washed with saline solution, dried with K$_2$CO$_3$ and concentrated arylphosphonyl dihalide. The residue was purified by column chromatography on silica gel using methylene chloride/hexane as an eluent to give the title compound as a solid: mp 158°–160° C.

Anal. Calc'd for C$_{18}$H$_{13}$Cl$_2$F$_5$N$_2$O$_4$S: C, 44.36; H, 2.69; N, 5.75 Found: C, 44.02; H, 2.68; N, 5.39

Example 36

3-(3,4-Dichlorophenyl)-1-(4-carbomethoxybenzesulfonyl)-1,4,5,6-tetrahydropyridazine (Compound 273)

A suspension of 3-(3,4-dichlorophenyl)-1-(4-carboxybenzenesulfonyl)-1,4,5,6-tetrahydropyridazine (prepared as described in Example 3) and acetyl chloride in methanol was heated to reflux for 6 hours, stirred at room temperature for 72 hours, heated to reflux for another 3 hours and concentrated. The residue was purified by column chromatography on silica gel using methylene chloride as an eluent to give the title compound as a solid: mp 146°–152° C.

Anal. Calc'd for C$_{18}$H$_{16}$Cl$_2$N$_2$O$_4$S: C, 50.58; H, 3.78; N, 6.55 Found: C, 50.58; H, 3.77; N, 6.42

Example 37

1-(4-Aminobenzenesulfonyl)-3-(3,4-dichlorophenyl)-1,4,5,6-tetrahydropyridazine (Compound 274)

(3,4-Dichlorophenyl)-1-(4-nitrobenzenesulfonyl)-1,4,5,6-tetrahydropyridazine (4.7 g, 11.3 mmol) was suspended in acetic acid at 80° C. Iron filings (3.17 g) were added to this suspension and the resulting reaction mixture was heated at 60°–80° C. until the TLC did not show any starting nitro compound. The mixture was filtered concentrated and purified by column chromatography and recrystallization to give the title compound as a solid: mp 232°–234° C.

Anal. Calc'd for C$_{16}$H$_{16}$Cl$_2$N$_3$O$_2$S: C, 50.00; H, 3.94; N, 10.93 Found: C, 49.81; H, 3.61; N, 10.59

Example 38

3-(3,4-Dichlorophenyl)-1-(4-methylsulfonylbenzenesulfonyl)-1,4,5,6-tetrahydropyridazine (Compound 2751)

The title compound was prepared as described in Example 6 starting with 3-(3,4-dichlorophenyl)-1-(4-thiomethylbenzenesulfonyl)-1,4,5,6-tetrahydropyridazine (0.29 g, 0.70 mmol) and MCPBA (0.36 g, 0.83 mmol) to give a solid: mp 181°–183° C.

Anal. Calc'd for C$_{17}$H$_{16}$Cl$_2$N$_2$O$_4$S$_2$: C, 45.64; H, 3.61; N, 6.26 Found: C, 45.58; H, 3.50; N, 6.17

Example 39

A solution of bromine (8.75 mL) in acetic acid (25 mL) was added dropwise to a mixture of ethyl 4-oxo-4-(4-aminophenyl)butyrate which is prepared as disclosed by M. Thyes et al., *J. Med Chem*, 26, 800 (1983), (30 g 135.7 mmol) and potassium thiocyanide (30.6 g) at room temperature under nitrogen. The resulting exothermic reaction was allowed to subside and the mixture was stirred for 15 minutes. The reaction was quenched with cold water and the resulting precipitate was filtered, washed with water and dried to give the intermediate thiocyanate as a solid (mp 140° C.). This solid was added to solution of sodium sulfate nonahydrate (70 g) in water (200 mL) and heated to reflux for 1 hour under nitrogen. The resulting mixture was cooled to −10° C. and acidified to pH 5 with acetic acid. Ethyl-4-oxo-4-(4-amino-3-mercaptophenyl)butyrate precipitated out of this mixture as a solid in 93% yield.

Ethyl-4-oxo-4-(4-amino-3-mercaptophenyl)butyrate (22.5 g) was added to a 0.13M sodium bicarbonate solution (300 mL). The mixture was cooled to 5° C. and chloroacetyl chloride (9 mL) was added dropwise. The resulting mixture was stirred at 5° C. for 15 minutes, heated to reflux for 30 min, cooled with ice-water and acidified to a pH of 2 with 6N HCl. Ethyl-4-oxo-1,4(2H)-benzothiazin-7-yl)butyrate precipitated out of this solution as a solid.

Sodium hydride (60 % in oil: 2.15 g) was added at room temperature under nitrogen to a stirred solution of ethyl-4-oxo-1,4(2H)-benzothiazin-7-yl)butyrate (10 g) in DMF (100 mL). After 20 minutes, methyl iodide (3.34 mL) was added and the reaction mixture was stirred for 2 hours at room temperature and cooled to 0° C. Ethyl-4-oxo-4-(3,4-dihydro-4-methyl-3-oxo-1,4(2H)-benzothiazin-7-yl) butyrate precipitated out of this solution as a solid (in 76% yield ) (mp 72°–73.5° C.). Anhydrous hydrazine (0.5 mL) was added to a suspension of ethyl-4-oxo-4-(3,4-dihydro-3-oxo-1,4(2H)-benzothiazin-7-yl)butyrate (1.0 g). The mixture was heated to reflux for 72 hours and cooled to yield ethyl-4-oxo-4-(3,4-dihydro-4-methyl-3-oxo-1,4(2H)-benzothiazin-7-yl)-2,3,4,5-tetrahydropyridazin-3-one as a solid (0.16 g) (mp 235°–237° C.).

MCPBA (6.47 g) was added to a solution of ethyl-4-oxo-4-(3,4-dihydro-4-methyl-3-oxo-1,4(2H)-benzothiazin-7-yl) butyrate (6.47 g) in 8methylene chloride at room temperature under nitrogen. The reaction mixture was stirred for 2 hours, concentrated and recrystallized from ether/ethyl acetate to give ethyl-4-oxo-4-(3,4-dihydro-4-methyl-1,1,3-trioxo-1,4(2H)-benzothiazin-7-yl)butyrate (4.79 g).

A solution of ethyl-4-oxo-4-(3,4-dihydro-4-methyl-1,1,3-trioxo-1,4(2H)-benzothiazin-7-yl)butyrate (4.79 g) and hydrazine (1 mL) was heated to reflux for 1 h under nitrogen. The reaction mixture was stirred overnight at room temperature to give ethyl-4-oxo-4-(3,4-dihydro-4-methyl-1,1,3-trioxo-1,4(2H)-benzothiazin-7-yl)-2,3,4,5-tetrahydropyridazin-3-one (2.95 g) as a solid.

Example 40

1-(4-Aminobenzenesulfonyl)-3-(3-trifluoromethyl-4-Chlorophenyl)-1,4,5,6-tetrahydropyridazine (Compound 277)

(4-chlorophenyl)-1-(4-nitrobenzenesulfonyl)-1,4,5,6-tetrahydropyridazine (2.12 g, 5.0 mmol) was suspended in acetic acid at 80° C. Iron filings (3.0 g) were added to this suspension and the resulting reaction mixture was heated at 80° C. for 30 minutes and filtered. The solvent was removed at reduced pressure and the residue taken up in methylene chloride and filtered through silica gel. The eluent was evaporated and the residue recrystallized from ether to give (0.9 g) the title compound: mp 205°–206° C.

Anal. Calc'd for $C_{16}H_{16}ClN_3O_2S$: C, 54.92; H, 4.61; N, 12.01 Found: C, 54.92; H, 4.64; N, 12.17

Example 41

3-(4,5-Dibromo-2-thienyl)-1-(4-iodobenzenesulfonyl)-1,4,5,6-tetrahydropyridazine (Compound 278)

2,3-Dibromothiophene (15.3 g, 63 mM) and succinic anhydride (63 g, 63 mM) were dissolved in nitrobenzene (250 mL) and the mixture cooled to 0° C. Aluminum chloride (18.4 g) was added to this mixture. The red mixture was kept below 10° C. for three hours. Water (38 mL) and HCl (9 mL) were added. The solution was extracted with 1M sodium hydroxide and the basic extracts were combined and washed with dichloromethane. The aqueous solution was then acidified with diluted HCl solution and extracted with dichloromethane. The organic solution was dried over magnesium sulfate, evaporated and the residue 4-(4,5-dibromo-2-thienyl)-4-oxobutyric acid (14.8 g) was dissolved in ethanol. Hydrazine (3.63 g) was added and the mixture was heated at reflux for 2 h. The mixture was cooled and the product collected by filtration and dried to give 11.3 g of 3-(4,5-dibromo-2-thienyl)-1,4,5,6-tetrahydropyridazin-6-one.

(4,5-Dibromo-2-thienyl)-1,4,5,6-tetrahydropyridazin-6-one (2.75 g, 8.14 mM) was dissolved in THF (80 mL) and diborane (1M in THF solution) (16.3 mL, 16.3 mM) added. After stirring the solution for 0.5 h the excess reagent was quenched with 20% sodium hydroxide solution and the mixture was filtered The filtrate was evaporated to give the pyridazine compound as a yellow oil (2.78 g) which was used in the next step without purification.

(4,5-Dibromo-2-thienyl)-1,4,5,6-tetrahydropyridazine (0.92 g, 2.83 mM) was dissolved in pyridine and pipsyl chloride (0.8 g, 2.83 nM) added to the solution. The mixture was stirred at room temperature for 3 hours then poured into 3N HCl and extracted with dichloromethane. The organic fraction was dried over magnesium sulfate and evaporated. The residue was chromatographed on silica gel and the fractions containing product were combined, evaporated to dryness, and recrystallized from methanol/chloroform giving 0.9 g of 3-(4,5-dibromo-2-thienyl)-1-(4-iodobenzenesulfonyl)-1,4,5,6-tetrahydropyridazine with mp 155°–156° C.

Anal. Calc'd for $C_{14}H_{11}Br_2IN_2O_2S_2$: C, 28.50; H, 1.88; N, 4.75 Found: C, 28.53; H, 1.90; N, 4.68.

Example 42

3-(5-Bromo-2-thienyl)-1-(3,4-dichlorobenzoyl)-1,4,5,6-tetrahydropyridazine (Compound 279)

(5-Bromo-2-thienyl)-1,4,5,6-tetrahydropyridazin-6-one was prepared as in Example 41 condensing 2-bromothiophene and succinic anhydride with aluminum chloride followed by reaction with hydrazine in ethanol.

(5-Bromo-2-thienyl)-1,4,5,6-tetrahydropyridazin-6-one (4.0 g, 15 mM) was dissolved in THF (80 mL) and diborane (1M in THF solution) (32 mL, 32 mM) was added. After stirring for 0.5 h the excess reagent was quenched with 20% sodium hydroxide solution and the mixture was filtered. The filtrate was evaporated to give the pyridazine as a yellow oil (3.92 g) which was used in the next step without purification.

(5-Bromo-2-thienyl)-1,4,5,6-tetrahydropyridazine (1.0 g, 4.1 mM) was dissolved in $CH_2Cl_2$ (40 mL) and 3,4-dichlorobenzoyl chloride (0.85 g, 4.1 mM) and trimethylamine (40 mL) were added to the solution. The mixture was stirred at 22° C. for 3 h then poured into 1N HCl. The organic layer was dried over $MgSO_4$ and evaporated. The residue was recrystallized from methanol/IPA to give 0.9 g of product with mp 138°–140° C.

Anal. Calc'd for $C_{15}H_{11}BrCl_2N_2OS$: C, 43.09; H, 2.65; N, 6.70 Found: C, 43.30; H, 2.73; N, 6.60

Example 43

3-(2-Thienyl)-1-(3,4-dichlorobenzoyl)-1,4,5,6-tetrahydropyridazine (Compound 280)

(2-Thienyl)-1,4,5,6-tetrahydropyridazin-6-one (4.0 g, 22 mM) was dissolved in THF and lithium aluminum hydride (40 mL, 1N solution in THF) was added at 15° C. The mixture was allowed to warm to room temperature and stir for 1 h. Excess reagent was destroyed with 15% sodium hydroxide and the mixture was filtered and evaporated to dryness to give 3.0 g of a light yellow oil which crystallized upon standing in air.

(2-Thienyl)-1,4,5,6-tetrahydropyridazine (1.0 g, 5.56 mM) was dissolved in dichloromethane (150 mL) and triethylamine (100 mL) was added followed by 3,4-dichlorobenzoyl chloride (1.17 g, 5.56 mM). The mixture was stirred at room temperature for 18 h and evaporated to dryness. The residue was chromatographed on silica gel and eluted with $CH_2Cl_2$ to give 1.1 g of white solid with mp 124°–125° C.

Anal. Calc'd for $C_{15}H_{12}Cl_2N_2OS$: C, 53.11; H, 3.56; N, 8.26 Found: C, 52.75; H, 3.54; N, 7.91.

Example 44

1-(4-Iodobenzenesulfonyl)-3-(3-trifluoromethyl-4-chlorophenyl)-6-methyl-1,4,5,6-tetrahydropyridazine (Compound 281)

4-Phenylurazole (4.74 g, 0.027 mmol) was dissolved in dry DMSO and cooled to 10° C. under nitrogen. Tosylisocyanate (5.39 g, 0.027 mmol) was added and the mixture allowed to come to room temperature. 4-Chloro-3-trifluoromethylphenyl-1,3-pentadiene was added slowly while the solution was cooled to 15° C. After 30 min the reaction was diluted with chloroform (500 mL) and washed with 5% NaOH solution. The organic layer was dried over magnesium sulfate and filtered. The solvent was removed at reduced pressure and the residue used in the next step.

The above residue (3.0 g) was dissolved in THF and one equivalent of diborane added slowly at 0° C. When addition was complete the mixture was heated to 45° C. for 2 h. Propionic acid was added and the temperature raised to 80° C. for 1.5 h. Water and saturated $NaHCO_3$ solution was added and the mixture extracted with ether and dichloromethane. The combined organic layers were dried over $Na_2SO_4$, filtered and evaporated to dryness.

The above residue (1 g) was dissolved in ethylene glycol and five equivalent of potassium hydroxide and heated to 110° C. for 3 h. Water (400 mL) was added and the mixture extracted with ether and dichloromethane. After drying ($Na_2SO_4$) and filtration, the solvent was removed at reduced pressure to give 700 mg of product.

3-(3-trifluoromethyl-4-chlorophenyl)-6-methyl-1,4,5,6-tetrahydropyridazine (700 mg) was combined with 4-iodobenzenesulfonyl chloride (558 mg) and heated to 105° C. for 3 h. Dichloromethane was added and the solution washed with water, 10% HCl, sat'd $NaHCO_3$ and brine. The organic layer was dried ($Na_2SO_4$), filtered and solvent removed at reduced pressure to give a residue which was recrystallized from acetone/hexane to give 148 mg of the title compound with mp 157°–158° C.

Anal. Calc'd for $C_{18}H_{15}ClF3IN_2O_2S$: C, 39.83; H, 2.79; N, 5.16

C, 39.56; H, 2.65; N, 5.19

Example 45

1-(4Iodobenzenesulfonyl)-3-(3,4-dichlorophenyl)-6-methyl 1,4,5,6-tetrahydropyridazine (Compound 282)

The method of example 44 was employed using 3,4-dichlorophenyl-1,3-pentadiene to give the desired product with mp 194°–196° C.

Anal. Calc'd for $C_{17}H_{15}Cl2IN_2O_2S$: C, 40.10; H, 2.97; N, 5.50 C, 39.97; H, 2.80; N, 5.46

Methods for the Determination of Progestational or Antiprogestational Activity

Progestin Receptor Binding

A progestin initiates a biological response by first binding to a progestin receptor. Affinity for progestin receptors was determined by measuring the ability of compounds to displace a progestin radioligand from those receptors in vitro. Cytosolic progestin receptor were obtained by mixing rabbit uterine tissue with a Tris buffer [0.1M Tris-Hcl, 1 mM $Na_2EDTA$, 1 mM dithiothreotol, 1 mM sodium molybdate, 1% glycerol, pH 7.4]. The tissue/buffer mixture was homogenized under ice-cold conditions. The homogenate was then centrifuged and the supernatant (cytosol preparation) was decanted and stored at −70° C. and thawed prior to use. The competitive binding assay was performed by mixing $^3$H-R5020, a progestin radioligand, with cytosol preparation and various concentrations of test compounds (prepared in DMSO with a final 5% DMSO concentration). This mixture was then incubated at 4° C. for about 18 hours. Non-specific binding was determined using an unlabelled ligand in excess. After the incubation period, the radioligand bound to receptor was separated from free radioligand using dextran-coated charcoal. The amount of bound radioligand was then determined by liquid scintillation counting. The data were expressed as the concentration of test compound that displaced 50% of the radioligand from the receptor ($IC_{50}$)

Aspects of the application used in this procedure are described in the following: J. L. McGuire et al., Biochemistry 13, 319, 1974.

Ex Vivo Progestational Test

The progestational activity of the compounds was accessed by their ability to stimulate proliferation of human breast carcinoma cells. Proliferation was measured as the ability to stimulate $^3$H-thymidine incorporation into these cells in vitro. Human T47D breast carcinoma cells (American Type Tissue Collection #133-HTB) were maintained in media consisting or RPMI 1640 supplemented with 10% fetal bovine serum, 10 ug/ml insulin, 10 U/ml pennicillin, 100 ug/ml streptomycin, and 2 mM L-glutamine. Monolayer cell cultures were trypsinized and washed in assay media consisting of phenol red-free RPMI 1640 supplemented with 5% charcoal-stripped, fetal bovine serum, and the other ingredients listed above. Cells were then plated in a 96-well plate. After a 48-hour incubation period at 37° C., the conditioned media was removed and replaced with fresh media containing test compounds in DMSO (0.1% DMSO final concentration). The cell cultures were incubated for 18 to 20 hours at 37° C. $^3$H-thymidine was then added to each well and the cell cultures were incubated at 37° C. for an additional 4 hours. Labelling was stopped by addition of un labelled thymidine. The cultures were washed twice, trypsinized and then harvested onto a filter mat. Incorporated $^3$-H-thymidine was measured by liquid scintillation counting. Data was expressed as a percent stimulation above control level which was set at 100%. An $SC_{200}$ value was calculated as the concentration of test material needed to stimulate $^3$H-thymidine incorporation 200% of control.

Aspects of the application of the procedure used are described in the following: C. Christensen, D. Gunter, D. Saunders and V. Malviya, Gynecol. Oncol., 28, 25 (1987); J.

Puzas, R. Drivdahl, G. Howard and D. Baylink, Proc. Soc. Exp. Biol. Med., 166, 113 (1981); and I. Keydar, L. Chen, S. Karby, F. Weiss, J. Delarea, M. Raduy, S. Chaitcik and H. Brenner, Eur. J. Cancer, 15, 659 (1979)

Ex Vivo Antiprogestational Test

The same test system as above may be used to determine antiprogestational activity by inducing a positive response with an appropriate amount of a standard progestin such as R5020 and diminishing that response with increasing concentrations of an antiprogestin. The concentration of antiprogestin needed to reduce the progestational activity by 50% is designated as the $ED_{50}$ concentration.

In Vivo Progestational Test (McGinty Test)

Progestational activity was measured in vivo by the ability to stimulate the rabbit endometrium after injection into the uterine horn.

Immature New Zealand White female rabbits were injected subcutaneously for 6 days with 5.0 µg of 17β-estradiol per day. On the 7th day the rabbits were anesthetized, the abdomen opened and a uterine horn exposed. Two ligatures were placed around a segment of the uterus 3–4 cm long, leaving the major blood vessels outside the ties.

The upper ligature was tied tightly, and the lower one was left loose. A needle attached to a syringe was injected in the uterus below the second ligature and up into the area between the two ligatures. As the test material was injected, the ligature was tightened and held tight so that the needle was withdrawn without the loss of fluid. The second ligature was secured and the abdomen closed.

The rabbits were sacrificed approximately 72 hours after the injection. The uteri were removed, fixed in 10% buffered formalin, sectioned at 6µ, and stained with hematoxylin and eosin. The evaluation for endometrial proliferation was made according to a McPhail Index. Each slide was graded for each rabbit on a 0 (no response)-4 (maximum response) scale. The compounds active in this assay are tabulated in Table 13.

Aspects of the application of the procedure used are described in the following: D. McGinty, C. Anderson, and N. McCullough, Endocrinology, 24, 829 (1939); M. McPhail, J. Physiol., 82, 145 (1934); and G. Pincus, and N. Werthessen, Am. J. Physiol., 120, 100 (1937).

In Vivo Progestational Test (Clauberg Test)

Progestational activity was also measured in vivo by the abiity to stimulate the rabbit endometrium after either oral or parenteral administration.

Immature New Zealand female White rabbits were primed with a daily subcutaneous injection, for 6 days, with 5 micrograms of 17β-estradiol in sesame oil. Starting on the 7th day, the rabbits were given the test material daily for five days. The rabbits were sacrificed approximately 24 hours after the last administration, and the uteri were excised, trimmed and weighed. Portions of both uterine horns were fixed in 10% neutral formalin, sectioned at 6µ and stained with hematoxylin and eosin. Progestational activity was assessed as described above for the McGinty Test. The compounds active in this assay are tabulated in Table 13

Aspects of the application used in this procedure are described in the following: M. K. McPhail, *J. Physiology* 83:145, (1934).

Method for the Determination of Bone Growth Activity Osteoblast Cell Proliferation Compounds of the present invention have utility to treat osteoporosis through enhancement of bone calcification rather than traditional approaches which generally involve inhibition of bone degeneration or resorption. The compounds of the present invention have been evaluated as stimulators of proliferation of osteoblast cell and chick calivaria bone organ culture which is predictive of enhancement of bone mass and bone formation in vivo.

The action of select compounds to stimulate osteoblast growth was measured in culture by estimating the rate of DNA synthesis by the rate of $^3$H-thymidine incorporation into DNA. Only cells undergoing mitosis synthesized new DNA and thus only these cells incorporated the radiolabelled DNA-specific thymidine. The stimulation of the proliferation and differentiation of bone-forming cells, osteoblasts, was a prerequisite for an increase in bone formation and bone mass. The ability of agents to increase osteoblast proliferation and differentiation can be predicted by their action on cultured osteoblast-line cells in vitro. In this test, mouse (MC3T3-E1) and human (TE-85) osteoblast-line cells (American Type Tissue Culture Collection, #CRL 1543, Rockville, Md. cloned by Sudo et al., Koriyama, Japan) were cultured in vitro and the effect of various agents were tested on osteoblast cell proliferation. Cells were harvested from large culture flasks where they were allowed to grow to near confluency using trypsin. The cells were plated into 96 well culture plates, 1600 cells in 100 µL per well in Dulbencos Modified Eagle's Medium (DMEM) with 25 mM HEPES buffer, L-glutamine (584 mg/L); D-glucose (4.5 g/L) supplemented with fetal bovine sera (10%); penicillin (100 units/mL) and streptomycin (100 mcg/mL); sodium pyruvate (10 µM final concentration). The cells were allowed to plate overnight in DMEM containing 10% fetal bovine sera at 37° C. in an atmosphere of 5% $CO_2$/95% air. Following their placement into 96 well culture plates all the osteoblast-line cells, either the MC3T3-E1 or the TE-85 cell lines, were allowed an additional 24 hours preincubation period in media containing only 0.1% fetal bovine sera.

The next day the test compounds were added and screened at concentrations ranging from $10^{-14}$ to $10^{-16}$M depending on the study. Twenty hours later, a 20 µL aliquot of media containing 0.4 µCi of $^3$H-thymidine was added to each culture well. The cells were then incubated an additional 4 hours. The incubation was terminated by aspirating the media and washing with HBSS (Hank's Balanced Salt Solution). The cells were then treated with 100 µL of 0.5% trypsin and 5.3 mM EDTA for 30 minutes at room temperature. The cells were then aspirated onto glass fiber filter and washed with water. The radioactivity on the filters was quantified by liquid scintillation spectroscopy. The rate of $^3$H-thymidine incorporation into DNA was then utilized as an index of cell proliferation. The results are shown in Table 13 expressed as % times control where the control is 100%. A value greater than 110 was considered statistically significant, and (provide more preferred values).

Aspects of the application of the procedure used are described in the following: J. E. Puzas, R. H. Drivdahl, A. G. Howard, and D. J. Baylink, Proc. Soc. Exper. Biol. Meal., 166, 113 (1981); and (provide other references).

Central Nervous System Receptor ($^{35}$S-TBPS(t-Butylphosphothionate)) Binding The biological test used to generate the data involves the binding of a ligand to a site on the $GABA_A$ receptor. The ligand is $^3$H-TBPS(tertbutylphosphothionate), which binds to a site within the $Cl^-$ channel domain of the receptor. Steroids affect the binding of $^3$H-TBPS to this site by inducing a conformational change in the receptor at a site allosteric to the TBPS binding site. This conformational change can either increase or decrease the binding of TBPS. GABA itself is known to have similar effects on TBPS binding. The effect of a particular steroid on TBPS binding to Central Nervous System (CNS) membrane preparations depends on what region of the CNS the membranes (receptors) are derived from. Further GABA can markedly affect the activity of asteroid. If GABA increases the potency (affinity) of asteroid, this is interpreted as an indication that the steroid has a positive modulatory effect on the activity of GABA. Such a compound is expected to be useful therapeutically for treating anxiety or epilepsy.

The procedure used to test the compounds of the present invention is essentially that of R. P. Shank and W. J. Baldy, J. Neurochem., 55, 541 (1990).

Procedure

Charles River, male Wistar rats (virus-free) (160–280 g) were used. The rats were group housed for approximately one week and given food and water ad libitum. Animals had equal hours of dark and light (12—12).

Test compounds (approximately 1 mg) were dissolved in the appropriate volume of distilled water to yield a 0.2 mM stock solution. Compounds that were not water soluble were dissolved in DMF (and/or NaOH or HCl) to a concentration of 20 mM, and then diluted to the stock concentration of 0.2 mM in distilled water. The stock solutions were then diluted in distilled water to the working concentrations used in the experiment.

Rats were sacrificed by cervical dislocation, and the brains were rapidly excised on an ice-cold parafilm-covered petri dish. Tissue from three areas of the brain was typically used: cerebral cortex, cerebellum, and brain stem (mesencephalon, medulla, and pons). The tissue from each area was homogenized in 20–40 volumes of NaHEPES (10 mM) buffered sucrose (0,3M) solution (made fresh weekly) with six full strokes on a motor-driven Teflon pestle/glass homogenizer. The homogenate was then centrifuged at 1000×g for 10 minutes and the resulting supernatant was recentrifuged at 42,000×g for 10 minutes. The supernatant from this spin was discarded. The resulting pellet was resuspended in 20–40 volumes of phosphate buffer and preincubated for 1 hour at 23° C. Following the incubation, the homogenate was centrifuged at 48,000×g for 10 minutes. The resulting pellet was resuspended in 25–30 volumes of 3 mM phosphate buffer (made fresh weekly by mixing 1M $K_2HPO_4$ (6 mL) into 1.5 L of distilled water, adjusting to a pH 7.4 with 1M $KH_2PO_4$, and extending to 2 L) and kept on ice.

Incubation Procedure

Each 13×100 mm glass tube received 1.25 mL phosphate buffer, 0.2 mL NaCl, 0.1 mL distilled water, 0.1 mL $^{35}S$-TBPS (working concentration of approximately 3 nM (4.5–5.0×$10^4$ DPM/0.1 mL)), 0.1 mL of the test compound and 0.25 mL of membrane suspension for a total volume of 2 mL. Samples tested in the presence of GABA received 0.1 mL of 0.02 mM GABA (made fresh) and no water. Typically, half of the samples received GABA. Control samples received an additional 0.1 mL of water in place of the test compound, and the blanks received 0.1 mL of the 2 mM GABA solution (made fresh). The reaction was stated by the addition of the membrane material. The samples, in groups of 12, are then immediately vortexed and incubated at 25° C. for 10 minutes. The reaction was terminated by rapid vacuum filtration through pre-wet LKB FG/B Filtermats mounted on a Skatron Cell Harvester designed to operate with the LKB Betaplate system. The samples were rinsed twice with approximately 2 mL of ice-cold 10 mM NaHEPES wash buffer (made fresh weekly). Following the filtration, the Filtermats were dried in a microwave oven (3 minutes each side). LKB Betaplate scintillation fluid (0.1 mL) was added to each of the 96 sample "spots" on the Filtermat which was then placed in a solvent-resistant plastic bag, heat sealed, and counted in an LKB Betaplate scintillation counter.

Data Analysis

The specific binding varies with the area of the brain, and typically represents approximately 78% of the total binding in the cortex, 64% in the cerebellum without GABA present, 55% in the cerebellum with GABA, and 52% in the brain stem. The nonspecific binding was determined using 10 µM GABA. The counts per minute (CPM's) for the blank are averaged and subtracted from the samples and controls. The CPM's for the samples and controls are then averaged.

Calculation of Percent Inhibition

Percent inhibition is calculated according to the equation:

$$\% I = 100 - \frac{(CPM \text{ for test compound} \times 100)}{CPM \text{ for control}}$$

TABLE 13

| | Osteoblast Cell Proliferation[1] | | | | | | Progestational Effect | | | |
|---|---|---|---|---|---|---|---|---|---|---|
| Cpd | $10^{-6}$ | $10^{-7}$ | $10^{-8}$ | $10^{-9}$ | $10^{-10}$ | GABA[2] | IC50[3] | T47D[4] | ED50[5] | In-vivo[6] |
| 1 | | | | | | 8.7 | 1.33 | 46 | | C,M |
| 2 | 105 | 119 | 99 | 91 | 77 | >11 | 3000 | | | |
| 3 | 92 | 110 | 115 | 138 | 118 | | 10000 | | | |
| 4 | 108 | 111 | 155 | 153 | 158 | | 201 | | | |
| 5 | 89 | 106 | 124 | 108 | 114 | | 5.3 | | 81 | |
| 6 | 81 | 97 | 106 | 114 | 121 | | 15 | | | |
| 9 | 65 | 94 | 128 | 102 | 119 | | 362 | | | |
| 10 | 91 | 90 | 123 | 115 | 139 | | 1050 | | | |
| 11 | 106 | 135 | 156 | 131 | 154 | | 20 | | | |
| 12 | 118 | 115 | 114 | 131 | 135 | 0.7 | 1 | 153 | | C,M |
| 13 | 88 | 109 | 114 | 109 | 152 | | 9 | | | |
| 14 | 96 | 109 | 118 | 136 | 139 | | 7 | | | |
| 15 | 94 | 108 | 114 | 123 | 123 | | 6.2 | 10000 | | |
| 16 | | | | | | | 4.2 | | | |
| 17 | | | | | | | 48 | | | |
| 18 | | | | | | | 204 | | | |
| 19 | | | | | | | 61 | | | |
| 20 | | | | | | | 56 | | | |
| 21 | | | | | | | 42 | 10000 | | |

TABLE 13-continued

| | Osteoblast Cell Proliferation[1] | | | | | | Progestational Effect | | | |
|---|---|---|---|---|---|---|---|---|---|---|
| Cpd | $10^{-6}$ | $10^{-7}$ | $10^{-8}$ | $10^{-9}$ | $10^{-10}$ | GABA[2] | IC50[3] | T47D[4] | ED50[5] | In-vivo[6] |
| 22 | 86 | 78 | 66 | 59 | 40 | | 0.54 | 10000 | 154 | |
| 23 | | | | | | | 3000 | | | |
| 24 | | | | | | | 308 | | | |
| 25 | 87 | 106 | 101 | 99 | 90 | | 49 | | | |
| 26 | | | | | | | 451 | | | |
| 27 | | | | | | | 65 | | | |
| 28 | | | | | | | 3140 | | | |
| 29 | | | | | | | 244 | | | |
| 30 | | | | | | | 22 | | | |
| 31 | | | | | | | 4 | | | |
| 32 | 89 | 103 | 105 | 111 | 118 | | 45 | | | |
| 33 | 96 | 107 | 117 | 127 | 152 | | 9 | | | |
| 34 | 87 | 102 | 105 | 114 | 114 | | 3 | | | M |
| 35 | 82 | 101 | 123 | 150 | 154 | | 3.01 | | | M |
| 36 | | | | | | | 11.5 | | | |
| 37 | | | | | | | 12.9 | | | |
| 38 | 76 | 73 | 54 | 49 | 37 | | 5.29 | | 545 | |
| 39 | 92 | 94 | 84 | 115 | 99 | 3.2 | 0.7 | 100 | | C,M |
| 40 | 78 | 90 | 71 | 58 | 53 | | 1.18 | 26 | | C,M |
| 41 | 138 | 158 | 166 | 144 | 116 | | 1.96 | 4000 | | M |
| 42 | 135 | 144 | 155 | 146 | 166 | | 0.97 | 321 | | M |
| 43 | 93 | 92 | 99 | 98 | 85 | | 3.3 | | | |
| 44 | 86 | 107 | 105 | 95 | 87 | | 30.8 | | | |
| 45 | 108 | 97 | 123 | 135 | 95 | | 14.2 | | | |
| 46 | | | | | | | 15.0 | | | |
| 47 | 109 | 112 | 113 | 115 | 123 | | 20.1 | | | |
| 48 | | | | | | | 266 | | | |
| 49 | | | | | | | 127 | | | |
| 50 | | | | | | | 316 | | | |
| 51 | 119 | 120 | 144 | 126 | 158 | | 203 | | | |
| 52 | | | | | | | 42 | | | |
| 53 | | | | | | | 2198 | | | |
| 54 | | | | | | | 780 | | | |
| 55 | | | | | | | 21.9 | | | |
| 56 | | | | | | | 85.2 | | | |
| 57 | | | | | | | 189 | | | |
| 58 | | | | | | | 444 | | | |
| 59 | | | | | | | 455 | | | |
| 60 | | | | | | | 191 | | | |
| 61 | | | | | | | 435 | | | |
| 62 | | | | | | | 157 | | | |
| 63 | 101 | 103 | 99 | 77 | 97 | | 118 | | | |
| 64 | 116 | 115 | 121 | 128 | 137 | >11 | 550 | | | |
| 65 | 90 | 98 | 94 | 88 | 80 | | 57 | | | |
| 66 | | | | | | | 375 | | | |
| 67 | | | | | | | 126 | | | |
| 68 | | | | | | | 13.4 | | | |
| 69 | | | | | | >11 | 10000 | 10000 | | |
| 70 | | | | | | >11 | 10000 | | | |
| 71 | 110 | 114 | 99 | 103 | 98 | 0.77 | 10000 | | | |
| 72 | 113 | 119 | 129 | 120 | 123 | >11 | 10000 | | | |
| 73 | | | | | | 3.4 | 10000 | 10000 | | |
| 74 | | | | | | 2.2 | 10000 | 10000 | | |
| 75 | | | | | | 0.21 | 10000 | | | |
| 76 | | | | | | 1.1 | 10000 | | | |
| 77 | | | | | | | 1.47 | 286 | | C,M |
| 78 | | | | | | | 2.44 | 10000 | | C,M |
| 79 | | | | | | | 0.9 | 10000 | 406 | |
| 80 | | | | | | | 0.79 | 85 | | M |
| 81 | | 110 | 119 | 119 | 128 | | 16.5 | | | |
| 82 | | | | | | | 2.95 | 608 | | M |
| 83 | | | | | | | 4.83 | | | |
| 84 | 108 | 119 | 130 | 127 | 122 | >11 | 1000 | | | |
| 85 | 99 | 80 | 76 | 54 | 48 | | 1000 | | | |
| 86 | 100 | 114 | 94 | 103 | 101 | >11 | 228 | | | |
| 87 | 120 | 115 | 125 | 117 | 127 | | 82.2 | | | |
| 88 | 97 | 109 | 89 | 74 | 62 | 1.08 | 10.2 | | | |
| 89 | 115 | 97 | 113 | 106 | 98 | | 21.6 | | | |
| 90 | 90 | 95 | 68 | 68 | 42 | >11 | 71.7 | | | |
| 91 | | | | | | | 2.39 | | 115 | |
| 92 | | | | | | | 23.9 | | | |
| 93 | | | | | | | 11.1 | | | |
| 94 | 110 | 85 | 90 | 110 | 130 | | 14.6 | | | |
| 95 | | | | | | | 10.2 | 10000 | | |
| 96 | | | | | | | 12.1 | | | |

TABLE 13-continued

| | Osteoblast Cell Proliferation[1] | | | | | | Progestational Effect | | | |
|---|---|---|---|---|---|---|---|---|---|---|
| Cpd | $10^{-6}$ | $10^{-7}$ | $10^{-8}$ | $10^{-9}$ | $10^{-10}$ | GABA[2] | IC50[3] | T47D[4] | ED50[5] | In-vivo[6] |
| 97 | | | | | | | 0.99 | 92 | | C |
| 98 | | | | | | | 2.5 | | | |
| 99 | | | | | | | 21 | | | |
| 100 | | | | | | | 23 | | | |
| 101 | | | | | | | 195 | | | |
| 102 | | | | | | | 9 | | | |
| 103 | | | | | | | 149 | | | |
| 104 | | | | | | | 0.85 | 76 | | |
| 105 | | | | | | | 1.87 | 1070 | 125 | |
| 106 | | | | | | | 7.11 | | | |
| 107 | | | | | | | 7.45 | | | |
| 108 | | | | | | | 3.35 | | | |
| 109 | | | | | | | 1.09 | 1620 | 10000 | |
| 111 | | | | | | | 16 | 10000 | | |
| 112 | 109 | 91 | 134 | 1169 | 119 | | 371 | | | |
| 113 | 66 | 94 | 102 | 102 | 90 | | 27.6 | | | |
| 114 | | | | | | | 6.5 | | | |
| 115 | | | | | | | 2.09 | 72 | | C |
| 116 | | | | | | | 8.77 | | | |
| 117 | | | | | | | 4.97 | | | |
| 118 | | | | | | | 5.56 | | | |
| 119 | | | | | | | 2.53 | 868 | | |
| 120 | | | | | | | 13.3 | 831 | | |
| 121 | 120 | 123 | 122 | 120 | 181 | | | | | |
| 122 | | | | | | | 47 | | | |
| 123 | | | | | | | 557 | | | |
| 125 | | | | | | 10 | 6.66 | 166 | | C |
| 126 | | | | | | | 7.14 | | | |
| 127 | | | | | | | 4.04 | | | |
| 128 | | | | | | | 14.2 | | | |
| 129 | | | | | | | 4.94 | | | |
| 130 | | | | | | | 2.31 | | | |
| 131 | | | | | | >11 | 17.4 | | | |
| 132 | | | | | | >11 | 7.5 | | 779 | |
| 136 | | | | | | | 70 | | 75 | |
| 138 | | | | | | | 341 | | | |
| 141 | | | | | | | 396 | | | |
| 142 | | | | | | | 1620 | | | |
| 143 | | | | | | | 1380 | | | |
| 144 | | 112 | 122 | 117 | 108 | | 71.7 | | | |
| 145 | | | | | | | 100 | | | |
| 146 | | | | | | | 1000 | | | |
| 152 | 87 | 123 | 124 | 149 | 161 | | 175 | | | |
| 153 | 85 | 115 | 83 | 99 | 103 | | 636 | | | |
| 154 | 97 | 111 | 107 | 124 | 115 | | 819 | | | |
| 156 | 127 | 124 | 126 | 136 | 183 | | 1000 | | | |
| 157 | 107 | 108 | 113 | 111 | 128 | | 750 | | | |
| 158 | 105 | 102 | 122 | 114 | 119 | | 3000 | | | |
| 159 | 97 | 100 | 91 | 97 | 105 | | 1383 | | | |
| 160 | | | | | | | 32 | | | |
| 161 | 76 | 95 | 113 | 122 | 112 | | 3000 | | | |
| 162 | | | | | | | 3 | | | |
| 167 | 126 | 109 | 136 | 144 | 165 | | 5.93 | | | |
| 168 | 67 | 82 | 82 | 76 | 109 | | | | | |
| 169 | 128 | 131 | 133 | 134 | 195 | | | | | |
| 170 | 68 | 98 | 108 | 108 | 108 | >11 | 2.15 | 4000 | | |
| 171 | 72 | 110 | 121 | 118 | 129 | | | | | |
| 172 | 134 | 108 | 103 | 106 | 113 | | 32 | | | |
| 174 | | | | | | | 22.8 | 10000 | | |
| 175 | | | | | | | 6.2 | | | |
| 176 | 59 | 94 | 109 | 113 | 109 | >11 | | | | |
| 177 | | | | | | | 528 | | | |
| 178 | | | | | | | 5.18 | 164 | | |
| 182 | 95 | 108 | 118 | 139 | 115 | >11 | 100000 | | | |
| 183 | 88 | 133 | 131 | 136 | 135 | | 100000 | | | |
| 184 | 84 | 102 | 113 | 146 | 131 | >11 | 100000 | | | |
| 185 | 98 | 136 | 147 | 131 | 128 | | 3560 | 10000 | | |
| 188 | 105 | 129 | 130 | 135 | 137 | | 100000 | | | |
| 189 | 89 | 112 | 98 | 122 | 128 | | 100000 | | | |
| 190 | 121 | 135 | 130 | 139 | 158 | | 100000 | | | |
| 191 | 86 | 133 | 126 | 133 | 123 | | 100000 | | | |
| 192 | 115 | 131 | 128 | 132 | 148 | | 100000 | | | |
| 193 | 107 | 161 | 162 | 190 | 208 | >11 | 10000 | | | |
| 194 | 93 | 130 | 136 | 138 | 144 | 10 | 100000 | | | |
| 195 | 103 | 114 | 125 | 127 | 136 | | 100000 | | | |

TABLE 13-continued

| | Osteoblast Cell Proliferation[1] | | | | | | Progestational Effect | | | |
|---|---|---|---|---|---|---|---|---|---|---|
| Cpd | $10^{-6}$ | $10^{-7}$ | $10^{-8}$ | $10^{-9}$ | $10^{-10}$ | GABA[2] | IC50[3] | T47D[4] | ED50[5] | In-vivo[6] |
| 196 | 102 | 97 | 102 | 92 | 104 | | 100000 | | | |
| 197 | 87 | 89 | 91 | 81 | 52 | | 100000 | | | |
| 198 | 94 | 97 | 112 | 99 | 85 | | 10000 | | | |
| 199 | 105 | 104 | 96 | 83 | 61 | | 100000 | | | |
| 200 | 97 | 109 | 107 | 120 | 88 | | 5000 | | | |
| 201 | 89 | 117 | 91 | 69 | 52 | | 100000 | | | |
| 202 | 98 | 108 | 110 | 116 | 128 | | 279 | | | |
| 203 | 73 | 85 | 102 | 98 | 106 | | 978 | | | |
| 204 | 79 | 109 | 105 | 101 | 109 | | 3000 | | | |
| 205 | 92 | 115 | 140 | 141 | 138 | | 263 | | | |
| 206 | 108 | 91 | 83 | 83 | 92 | | 473 | | | |
| 209 | | | | | | | 117 | | | |
| 213 | | | | | | | 326 | | | |
| 214 | | | | | | 0.87 | | | | |
| 216 | 105 | 108 | 105 | 96 | 100 | | 103 | | | |
| 217 | 86 | 87 | 91 | 72 | 52 | | 102 | | | |
| 218 | 112 | 115 | 119 | 107 | 109 | | 1984 | | | |
| 219 | 144 | 171 | 141 | 180 | 178 | | 946 | 10000 | | |
| 229 | | 104 | 86 | 99 | 114 | | | | | |
| 231 | | 115 | 103 | 145 | 133 | 0.3 | | | | |
| 232 | | 110 | 115 | 115 | 121 | | | | | |
| 233 | | 130 | 132 | 130 | 138 | | | | | |
| 234 | | 95 | 84 | 84 | 111 | | | | | |
| 235 | | 86 | 87 | 92 | 88 | | | | | |
| 236 | | 109 | 102 | 106 | 115 | | | | | |
| 237 | | 113 | 113 | 110 | 119 | 2.42 | | | | |
| 240 | | | | | | 10 | | | | |
| 242 | | | | | | | 12 | | | |
| 243 | | 118 | 92 | 96 | 89 | | | | | |
| 244 | | 119 | 134 | 129 | 144 | | | | | |
| 246 | | | | | | | 114 | | | |
| 247 | | 118 | 122 | 122 | 129 | | | | | |
| 248 | | 142 | 130 | 140 | 149 | | | | | |
| 251 | 109 | 104 | 111 | 91 | 111 | 0.5 | | | | |
| 252 | 75 | 86 | 79 | 97 | 86 | >11 | 10000 | | | |
| 253 | 151 | 124 | 143 | 142 | 157 | >11 | 688 | | | |
| 254 | 91 | 111 | 110 | 132 | 143 | 10 | 1340 | 10000 | | |
| 255 | 107 | 125 | 139 | 132 | 145 | 1.05 | 204 | | | |
| 256 | 97 | 100 | 104 | 128 | 116 | 1.4 | 95.5 | | | |
| 257 | 86 | 114 | 122 | 112 | 114 | 2.9 | 300 | | | |
| 258 | 107 | 107 | 108 | 107 | 98 | 10 | | | | |
| 259 | 116 | 96 | 102 | 121 | 106 | 9 | | | | |
| 260 | 100 | 115 | 105 | 99 | 90 | >11 | | | | |
| 261 | 98 | 105 | 95 | 100 | 111 | 6.6 | 131 | | | |
| 262 | 99 | 104 | 102 | 110 | 141 | 1.1 | 958 | | | |
| 263 | | | | | | 0.73 | | | | |
| 264 | | | | | | 6.4 | | | | |
| 265 | | 110 | 112 | 112 | 115 | | | | | |
| 272 | | | | | | | 329 | | | |
| 273 | | | | | | | 3.4 | | | |
| 274 | | | | | | | 204 | | | |
| 275 | | 145 | 153 | 128 | 136 | | | | | |
| 276 | | | | | | | 53.9 | | | |
| 278 | | | | | | | 1.0 | 85 | | C |
| 281 | | | | | | | 0.02 | 10 | | C |
| 282 | | | | | | | 0.2 | 10.5 | | C |

[1]Expressed in % increase in incorporation of $^3$H-thymidine over control (100%)
[2]Binding affinity for the GABA$_A$ receptor from rat brain in μM.
[3]Binding affinity for the progestin receptor from rabbit uterus. in nM.
[4]Concentration to elicit a 200% increase in T47D Human breast cell proliferation.
[5]Concentration to block the action of 0.15 nM R5020 by 50%
[6]C = Active in Clauberg Assay; M = Active in McGinty Assay Additional Test to Determine Bone Growth Activity Test compounds were orally administered once daily to mature female rabbits for 12 weeks. Bone density was measured by dual X-ray densitometry and results were expressed as % base line bone mineral content.

Compounds 185 and 280 showed a significant increase in bone mineral content as compared to vehicle treated control.

I claim:

1. Compounds effective as progestin agonists and having the formula:

51

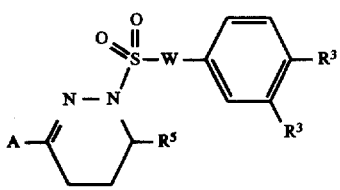

wherein:

A is

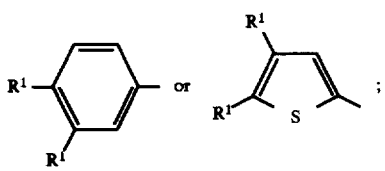

W is absent or —CH=CH—;

R¹ are independently selected from the group consisting of halogen, —CF₃, and NO₂, or both R¹ may be joined to form a bi-radical which is —CH=CHCH=CH—;

R³ are independently selected from the group consisting of hydrogen, $C_{1-6}$ branched or linear alkyl, halogen and —CF₃, with the proviso that R³ at the 3-position must be H when R³ at the 4-position is H, or both R³ may be joined to form a bi-radical selected from the group consisting of —CH=CHCH=CH—, —C(NC₁₋₄alkyl₂)=CHCH=CH— and —(CH₂)₄—;

R⁵ is selected from the group consisting of H and Me;

with the proviso that only one of R¹ and R³ forms the fused bi-radical; and the stereoisomers thereof.

2. The compound of claim 1 wherein said A is 4-R¹, 3-R¹-phenyl.

3. The compound of claim 1 where R³ is a mono-substituent at the 4-position and selected from the group consisting of $C_{1-6}$ branched or linear alkyl, halogen and —CF₃.

4. A compound of claim 1 selected from the group consisting of: 3-(naphth-2-yl)-1-(4-iodobenzenesulphonyl)-1,4,5,6-tetrahydropyridazine; 3-(3,4-dichlorophenyl)-1-(4-trifluoromethylbenzenesulphonyl)-1,4,5,6-tetrahydropyridazine; 3-(3,4-dichlorophenyl)-1-(4-iodobenzenesulphonyl)-1,4,5,6-tetrahydropyridazine; 3-(3,4-dichlorophenyl)-1-(4-chlorobenzenesulphonyl)-1,4,5,6-tetrahydropyridazine; 3-(3,4-dichlorophenyl)-1-(2-naphthylenesulfonyl)-1,4,5,6-tetrahydropyridazine; 3-(3,4-dichlorophenyl)-1-(4-bromobenzenesulphonyl)-1,4,5,6-tetrahydropyridazine; 3-(3,4-dichlorophenyl)-1-(4-methylbenzenesulphonyl)-1,4,5,6-tetrahydropyridazine; 3-(4-chloro-3-trifluoromethylphenyl)-1-(4-trifluoromethylbenzenesulphonyl)-1,4,5,6-tetrahydropyridazine; 3-(4-chloro-3-trifluoromethylphenyl)-1-(4-bromobenzenesulphonyl)-1,4,5,6-tetrahydropyridazine; 3-(4-chloro-3-trifluoromethylphenyl)-1-(4-iodobenzenesulphonyl)-1,4,5,6-tetrahydropyridazine; (R,S) 3-(3,4-dichlorophenyl)-1-(4-iodobenzenesulphonyl)-6-methyl-1,4,5,6-tetrahydropyridazine and (R,S) 3-(4-chloro-3-trifluoromethylphenyl)-1-(4-iodobenzenesulphonyl)-6-methyl-1,4,5,6-tetrahydropyridazine.

5. Compounds effective as progestin antagonists and having the formula:

52

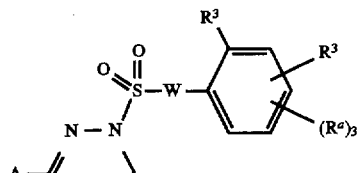

wherein

A is

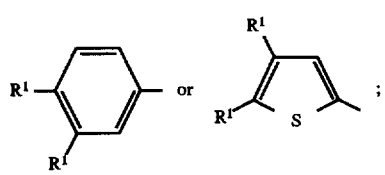

W is absent or —CH=CH—;

R¹ is selected from the group consisting of halogen, —CF₃ and —NO₂, or both R¹ may be joined to form a bi-radical which is —CH=CHCH=CH—;

R³ is hydrogen, halogen, —CF₃, $C_{1-4}$ alkyl, $C_{1-4}$ alkoxy, carboxy $C_{1-4}$ alkyl and $C_{1-4}$ alkoxy carbonyl $C_{1-4}$ alkoxy with the proviso that R³ at the 2-position is not hydrogen, or R³ may be joined to form a bi-radical which is —CH=CHCH=CH— attached at the 2- and 3-positions;

$R^a$ are independently selected from hydrogen or halogen with the proviso that each may be halogen when R³ is selected only from halogen;

R⁵ is selected from the group consisting of hydrogen and methyl, or alternatively, R⁵ may be joined with the 6-position to form a bi-radical which is (5)-CH₂CH=CH-(6);

with the proviso that only one of R¹, R³ and R⁵ forms the fused bi-radical; and the steroisomers and pharmaceutically acceptable salts or esters thereof.

6. The compound of claim 5 wherein said A is 4-R¹, 3-R¹-phenyl.

7. The compound of claim 5 wherein R³ is a mono-substitutent at the 2-position and selected from the group consisting of halogen CF₃, $C_{1-4}$ alkyl, $C_{1-4}$ alkoxy, carboxy $C_{1-4}$ alkyl and $C_{1-4}$ alkoxy carbonyl $C_{1-4}$ alkoxy.

8. A compound of claim 5 selected from the group consisting of:

3-(3,4-dichlorophenyl)-1-(2,3-dichlorobenzenesulphonyl)-1,4,5,6-tetrahydropyridazine; 3-(3,4-dichlorophenyl)-1-(2,5-dichlorobenzenesulphonyl)-1,4,5,6-tetrahydropyridazine; 3-(3,4-dichlorophenyl)-1-(2-(3-carbomethoxypropxy)-5-bromobenzenesulphonyl)-1,4,5,6-tetrahydropyridazine; 3-(4-chloro-3-trifluoromethylphenyl)-1-(2,5-dichlorobenzenesulphonyl)-1,4,5,6-tetrahydropyridazine and (R,S) 3-(3,4-dichlorophenyl)-1-(2,5-dichlorobenzenesulphonyl)-5-methyl-1,4,5,6-tetrahydropyridazine.

9. Compounds effective to promote bone cell growth and having the formula:

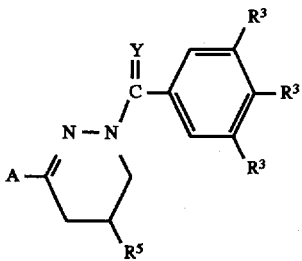

wherein

A is

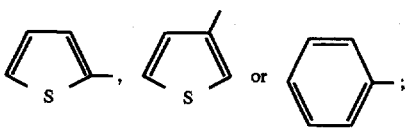

Y is O or S;

R³ is hydrogen or halogen with the proviso that at least two R³ are halogen;

R⁵ is H or Me;

and the steroisomers thereof.

10. The compound of claim 9 wherein said A is phenyl.

11. The compound of claim 9 wherein R₃ is at the 3- and 4-positions only.

12. A compound of claim 9 selected from the group consisting of:

1-(3,4-dichlorobenzoyl)-3-phenyl-1,4,5,6-tetrahydropyridazine; 1-(3,4-dichlorothiobenzoyl)-3-phenyl-1,4,5,6-tetrahydropyridazine; 1-(3,4-difluorothiobenzoyl)-3-phenyl-1,4,5,6-tetrahydropyridazine; 1-(3-bromo-4-fluorothiobenzoyl)-3-phenyl-1,4,5,6-1tetrahydropyridazine; (R,S)-(3,4-difluorobenzoyl)-5-methyl-3-phenyl-1,4,5,6-tetrahydropyridazine; (R,S)-1-(3,4-dichlorobenzoyl)-5-methyl-3-phenyl-1,4,5,6-tetrahydropyridazine; (R,S)-1-(3,4-dichlorothiobenzoyl)-5-methyl-3-phenyl-1,4,5,6-tetrahydropyridazine; (R,S)-1-(3,4-difluorothiobenzoyl)-5-methyl-3-phenyl-1,4,5,6-tetrahydropyridazine 1-(3,4-dichlorobenzoyl)-3-(thien-2-yl)-1,4,5,6-tetrahydropyridazine; 1-(3,4-dichlorobenzoyl)-3-(thien-3-yl)-1,4,5,6-tetrahydropyridazine; 1-(3,4-dichlorothiobenzoyl)-3-(thien-2-yl)-1,4,5,6-tetrahydropyridazine and 1-(3,4-dichlorothiobenzoyl)-3-(thien-3-yl)-1,4,5,6-tetrahydropyridazine.

* * * * *